(12) United States Patent
Schäfer et al.

(10) Patent No.: US 12,073,926 B2
(45) Date of Patent: Aug. 27, 2024

(54) DETECTING AND MONITORING ORAL ANTICOAGULANTS OR INTRAVENOUS DIRECT THROMBIN INHIBITORS IN A BLOOD SAMPLE

(71) Applicant: Instrumentation Laboratory Company, Bedford, MA (US)

(72) Inventors: Simon Schäfer, Munich (DE); Philipp Groene, Bad Feilnbach (DE); Klaus Görlinger, Kirchheim bei München (DE)

(73) Assignee: Instrumentation Laboratory Company, Bedford, MA (US)

(*) Notice: Subject to any disclaimer, the term of this patent is extended or adjusted under 35 U.S.C. 154(b) by 320 days.

(21) Appl. No.: 17/480,485

(22) Filed: Sep. 21, 2021

(65) Prior Publication Data
US 2022/0093223 A1    Mar. 24, 2022

Related U.S. Application Data

(60) Provisional application No. 63/091,018, filed on Oct. 13, 2020, provisional application No. 63/080,944, filed on Sep. 21, 2020.

(51) Int. Cl.
| | | |
|---|---|---|
| *G16H 10/40* | (2018.01) | |
| *G01N 11/00* | (2006.01) | |
| *G01N 33/49* | (2006.01) | |

(52) U.S. Cl.
CPC .............. *G16H 10/40* (2018.01); *G01N 11/00* (2013.01); *G01N 33/49* (2013.01)

(58) Field of Classification Search
CPC ........ G16H 10/40; G16H 50/20; G16H 20/10; G01N 11/00; G01N 33/49; G01N 33/86
See application file for complete search history.

(56) References Cited

U.S. PATENT DOCUMENTS

| | | |
|---|---|---|
| 5,120,537 A | 6/1992 | Esmon et al. |
| 5,187,155 A | 2/1993 | Fair |
| | (Continued) | |

FOREIGN PATENT DOCUMENTS

| | | |
|---|---|---|
| AU | 2015315159 | 11/2018 |
| AU | 2016264649 | 11/2018 |
| | (Continued) | |

OTHER PUBLICATIONS

Robert C. Gosselin, Jonathan Douxfils, Ecarin based coagulation testing, Jul. 2020, PubMed.ncbi.nlm.nih.gov, http://wileyonlinelibrary.com/journal/ajh, pp. 863-869 (Year: 2020).*

(Continued)

*Primary Examiner* — Francis C Gray
(74) *Attorney, Agent, or Firm* — ArentFox Schiff LLP

(57) ABSTRACT

An example method detecting a presence of one or more oral anticoagulants or intravenous (IV) direct thrombin inhibitors in a blood sample may include the following operations: receiving parameters that are based on viscoelastic tests; comparing the parameters to predefined threshold values, where the parameters and the predefined threshold values are based on an identity of the one or more oral anticoagulants or the IV direct thrombin inhibitors; and detecting, based on the comparing, the presence of the one or more oral anticoagulants or IV direct thrombin inhibitors in the blood sample. The viscoelastic tests are performed on portions of the blood sample to obtain the parameters. The viscoelastic tests include both a viscoelastic test based on Ecarin activation and a viscoelastic test with low tissue factor activation.

20 Claims, 4 Drawing Sheets

(56) References Cited

U.S. PATENT DOCUMENTS

| | | | |
|---|---|---|---|
| 5,547,850 A | 8/1996 | Nowak et al. | |
| 6,060,300 A | 5/2000 | Raditsch et al. | |
| 6,103,888 A | 8/2000 | Larrick et al. | |
| 6,245,573 B1 * | 6/2001 | Spillert | C12Q 1/56 |
| | | | 422/430 |
| 6,489,289 B2 | 12/2002 | Nortersheuser et al. | |
| 7,220,553 B2 | 5/2007 | Chu | |
| 7,294,479 B2 | 11/2007 | Yin | |
| 7,803,570 B2 | 9/2010 | Nowak et al. | |
| 8,008,086 B2 | 8/2011 | Cohen et al. | |
| 8,153,590 B2 | 4/2012 | Lu et al. | |
| 8,268,783 B2 | 9/2012 | Sinha et al. | |
| 8,455,439 B2 | 6/2013 | Lu et al. | |
| 8,455,441 B2 | 6/2013 | Lu et al. | |
| 8,685,636 B2 | 4/2014 | Braun et al. | |
| 8,889,129 B2 | 11/2014 | Lu et al. | |
| 8,889,370 B2 | 11/2014 | Kappel et al. | |
| 9,056,106 B2 | 6/2015 | Sinha et al. | |
| 9,062,298 B2 | 6/2015 | Lu et al. | |
| 9,109,046 B2 | 8/2015 | Sinha et al. | |
| 9,217,027 B2 * | 12/2015 | Kazimtrova | C07K 7/08 |
| 9,329,192 B2 | 5/2016 | Kolde et al. | |
| 9,388,401 B2 | 7/2016 | Lu et al. | |
| 9,587,233 B2 | 3/2017 | Sinha et al. | |
| 9,594,042 B2 | 3/2017 | Doerge et al. | |
| 9,700,603 B2 | 7/2017 | Plantier et al. | |
| 9,810,701 B2 | 11/2017 | Harenberg et al. | |
| 9,897,617 B2 | 2/2018 | Harenberg et al. | |
| 9,989,532 B2 | 6/2018 | Monroe et al. | |
| 10,147,152 B2 | 12/2018 | Viola et al. | |
| 10,161,944 B2 | 12/2018 | Viola et al. | |
| 10,175,225 B2 | 1/2019 | McCluskey et al. | |
| 10,191,031 B2 | 1/2019 | Nadkarmi et al. | |
| 10,234,469 B2 | 3/2019 | Hayashi et al. | |
| 10,288,541 B2 | 5/2019 | Hadj et al. | |
| 10,288,630 B2 | 5/2019 | Gorin et al. | |
| 10,337,048 B2 | 7/2019 | Ackermann et al. | |
| 10,357,769 B2 | 7/2019 | Delmenico et al. | |
| 10,481,168 B2 | 11/2019 | Viola et al. | |
| 10,495,613 B2 | 12/2019 | Walker et al. | |
| 10,501,773 B2 | 12/2019 | Zaman et al. | |
| 10,539,579 B2 | 1/2020 | Gorin et al. | |
| 10,613,104 B2 | 4/2020 | Ranby et al. | |
| 2003/0064414 A1 * | 4/2003 | Benecky | C12Q 1/56 |
| | | | 435/13 |
| 2008/0261261 A1 * | 10/2008 | Grimes | G01N 33/4905 |
| | | | 435/287.1 |
| 2015/0316460 A1 * | 11/2015 | Redl | G01N 33/5064 |
| | | | 435/287.9 |
| 2016/0032355 A1 * | 2/2016 | Zaman | C12Q 1/56 |
| | | | 435/13 |
| 2016/0091516 A1 | 3/2016 | Gorin et al. | |
| 2018/0177826 A1 * | 6/2018 | Nielsen | A61K 31/295 |
| 2018/0321265 A1 | 11/2018 | DiTullio et al. | |
| 2019/0113500 A1 | 4/2019 | McCluskey et al. | |
| 2019/0195898 A1 | 6/2019 | Schubert et al. | |
| 2019/0244692 A1 | 8/2019 | Viola et al. | |
| 2019/0283020 A1 | 9/2019 | Delemico et al. | |
| 2019/0353672 A1 | 11/2019 | Schubert et al. | |
| 2019/0353673 A1 | 11/2019 | Schubert et al. | |
| 2020/0057085 A1 | 2/2020 | Wasson et al. | |
| 2020/0063184 A1 | 2/2020 | Zaman et al. | |
| 2020/0081023 A1 | 3/2020 | Holmes et al. | |
| 2020/0116673 A1 | 4/2020 | Walker et al. | |
| 2020/0116742 A1 | 4/2020 | Gorin et al. | |
| 2022/0093223 A1 | 3/2022 | Schaefer et al. | |

FOREIGN PATENT DOCUMENTS

| | | |
|---|---|---|
| AU | 2016316202 | 11/2018 |
| AU | 2016316281 | 11/2018 |
| AU | 2017248548 | 12/2018 |
| AU | 2017213588 | 1/2019 |
| AU | 2019201621 | 4/2019 |
| AU | 2017272312 | 7/2019 |
| AU | 2018217311 | 9/2019 |
| AU | 2016364931 | 10/2019 |
| AU | 2019272053 | 12/2019 |
| AU | 2014227711 | 4/2020 |
| CA | 2740904 | 1/2019 |
| CA | 2911873 | 1/2019 |
| CA | 2979838 | 5/2019 |
| CA | 2959742 | 8/2019 |
| CA | 2731664 | 3/2020 |
| EP | 3001196 | 9/2018 |
| EP | 3383473 | 10/2018 |
| EP | 3014282 | 3/2019 |
| EP | 3457131 | 3/2019 |
| EP | 2555704 | 5/2019 |
| EP | 2965478 | 5/2019 |
| EP | 3175245 | 5/2019 |
| EP | 3483735 | 5/2019 |
| EP | 3146347 | 7/2019 |
| EP | 2375244 | 10/2019 |
| EP | 3595246 | 1/2020 |
| EP | 3611507 | 2/2020 |
| EP | 3620780 | 3/2020 |
| WO | 2017096284 | 6/2017 |

OTHER PUBLICATIONS

Adelmann et al., "Measuring the activity of apixaban and rivaroxaban with rotational thrombelastometry," Thromb Res. 134(4):918-23 (2014), 6 pages.

Akman et al., "Reversal of dabigatran by intraosseous or intravenous idarucizumab in a porcine polytrauma model," British Journal of Anaesthesia 120(5), pp. 978-987 (2018), 10 pages.

Amiral et al., "An update on laboratory measurements of Dabigatran: Smart specific and calibrated dedicated assays for measuring anti-IIa activity in plasma," Transfus. Apher. Sci. 54(3):428-437 (2016), 10 pages.

Arellano-Rodrigo et al., "Coagulation Factor Concentrates Fail to Restore Alterations in Fibrin Formation Caused by Rivaroxaban or Dabigatran in Studies with Flowing Blood from Treated Healthy Volunteers," Transfus Med Rev. 29(4):242-9 (2015), 8 pages.

Arellano-Rodrigo et al., "Idarucizumab, but not procoagulant concentrates, fully restores dabigatran-altered platelet and fibrin components of hemostasis," Transfusion 59(7):2436-2445 (2019), 10 pages.

Artang et al., "Fully automated thromboelastograph TEG 6s to measure anticoagulant effects of direct oral anticoagulants in healthy male volunteers," Res Pract Thromb Haemost. 3(3):391-396, DOI: 10.1002/rth2.12206 (2019), 6 pages.

Aranda et al., "Diagnostic accuracy of thromboelastometry and its correlation with the HPLC-MS/MS quantification test," Braz J Med Biol Res. 52(4):e8006, DOI: 10.1590/1414-431X20198006 (2019), 9 pages.

Bar et al., "Assessing Coagulation by Rotational Thromboelastometry (ROTEM) in Rivaroxaban-Anticoagulated Blood Using Hemostatic Agents," Prehospital and Disaster Med. 32(5):580-587, DOI: 10.1017/S1049023X17006641 (2017), 8 pages.

Becattini et al., "Old and new oral anticoagulants for venous thromboembolism and atrial fibrillation: a review of the literature," Thromb. Res. 129(3):392-400 (2012), 9 pages.

Beiderlinden et al., "Monitoring of argatroban and lepirudin anticoagulation in critically ill patients by conventional laboratory parameters and rotational thromboelastometry—a prospectively controlled randomized double-blind clinical trial," BMC Anesthesiol. 18(1):18 (2018), 15 pages.

Beynon et al., "Rivaroxaban and intracranial haemorrhage after mild traumatic brain injury: A dangerous combination?" Clinical Neurology and Neurosurgery, vol. 136, pp. 73-78 (2015), 6 pages.

Billoir et al., "Anti-Xa oral anticoagulant plasma concentration assay in real life: Rivaroxaban and Apixaban quantification in emergency with LMWH calibrator," Annals of Pharmacotherapy, vol. 53, No. 4, pp. 341-347, (2018), 7 pages.

(56) References Cited

OTHER PUBLICATIONS

Bliden et al., "Determination of non-Vitamin K oral anticoagulant (NOAC) effects using a new-generation thrombelastography TEG 6s system," J. Thromb. Thrombolysis, vol. 43, pp. 437-445 (2017), 9 pages.
Boyd et al., "Defining, Establishing, and Verifying Reference Intervals in the Clinical Laboratory; Approved Guidelines," CLSI document C28-A3, vol. 28, No. 3. 2010.
Božič-Mijovski et al., "Rotational thromboelastometry in ex vivo samples from routine clinical practice patients receiving dabigatran," Clin Chim Acta. 466:20-21 (2017), 2 pages.
Braun et al., "Platelet function and coagulation in patients with STEMI and peri-interventional clopidogrel plus heparin vs. prasugrel plus bivalirudin therapy (BRAVE 4 substudy)," Thromb Res. 137:72-8 (2016), 7 pages.
Brauckmann et al., "Lipopolysaccharide-Induced Hemolysis Is Abolished by Inhibition of Thrombin Generation but Not Inhibition of Platelet Aggregation," Inflammation 42(5):1767-1776, DOI: 10.1007/s10753-019-01038-6 (2019), 10 pages.
Breimann et al., "Classification and Regression Trees," Taylor & Francis Ltd; Auflage: UK ed., 1984, 366 pages.
Casutt et al., "Effect of rivaroxaban on blood coagulation using the viscoelastic coagulation test ROTEM™," Anaesthesist. 61, pp. 948-953 (2012), 6 pages.
Cate, H. T., "Testing direct oral anticoagulants: embedding in structured long-term care," Blood Transfus., 16, pp. 410-412 (2018), 3 pages.
Cate et al., "Direct oral anticoagulants: When to consider laboratory testing?" Int J Lab Hematol. 40, Suppl 1:30-33, DOI: 10.1111/ijlh.12816 (2018), 4 pages.
Cate et al., "Practical guidance on the use of laboratory testing in the management of bleeding in patients receiving direct oral anticoagulants," Vasc Health Risk Manag. 13:457-467, DOI: 10.2147/VHRM.S126265 (2017), 11 pages.
Chappell et al., "Hypervolemia increases release of atrial natriuretic peptide and shedding of the endothelial glycocalyx," Crit Care 18: 538, DOI: 10.1186/s13054-014-0538-5 (2014), 8 pages.
Chojnowski et al., "Effects of rivaroxaban therapy on ROTEM coagulation parameters in patients with venous thromboembolism," Adv. Clin. Exp. Med. 24(6), pp. 995-1000 (2015), 6 pages.
Comuth et al., "Comprehensive characteristics of the anticoagulant activity of dabigatran in relation to its plasma concentration," Thromb. Res. 164, pp. 32-39 (2018), 35 pages.
Connolly et al. for the ANNEXA-4 Investigators, "Andexanet alfa for acute major bleeding associated with factor Xa inhibitors," N. Engl. J. Med. 375(12), pp. 1131-1141 (2016), 11 pages.
Connors, J.M., "Testing and monitoring direct oral anticoagulants," Blood 132(19), pp. 2009-2015 (2018), 7 pages.
Crapelli et al., "A case of fatal bleeding following emergency surgery on an ascending aorta intramural hematoma in a patient taking Dabigatran," Journal of Cardiothoracic and Vascular Anesthesia, vol. 30, No. 4, pp. 1027-1031 (2016), 5 pages.
Dinkelaar et al., "Global coagulation tests: Their applicability for measuring direct factor Xa- and thrombin inhibition and reversal of anticoagulation by prothrombin complex concentrate," Clin. Chem. Lab. Med. 52(11), pp. 1615-1623 (2014), 9 pages.
Douxfils et al., "Laboratory testing in patients treated with direct oral anticoagulants: a practical guide for clinicians," J. Thromb. Haemost. 16, pp. 209-219, (2018), 11 pages.
Ebner et al., "Limitations of Specific Coagulation Tests for Direct Oral Anticoagulants: A Critical Analysis," J Am Heart Assoc. 7(19):e009807, DOI: 10.1161/JAHA.118.009807 (2018), 11 pages.
Ellenberger et al., "Assessment of Haemostasis in patients undergoing emergent neurosurgery by rotational Elastometry and standard coagulation tests: a prospective observational study," BMC Anesthesiol 17:146, DOI:10.1186/s12871-017-0440-1 (2017), 11 pages.
Eller et al., "Dabigatran, rivaroxaban, apixaban, argatroban and fondaparinux and their effecs on coagulation POC and platelet function tests," Clin. Chem. Lab. Med. 52(6), pp. 835-844 (2014), 10 pages.
Engberink et al., "Rapid and correct prediction of thrombocytopenia and hypofibrinogenemia with rotational thromboelastometry in cardiac surgery," J. Cardiothorac. Vasc. Anesth. 28(2), pp. 210-216 (2014), 18 pages.
Engstrom et al., "An evaluation of monitoring possibilities of argatroban using rotational thromboelastometry and activated partial thromboplastin time," Acta Anaesthesiol Scand. 54(1):86-91, DOI: 10.1111/j.1399-6576.2009.02082.x (2010), 6 pages.
Erber et al., "Development of cryopelletization and formulation measures to improve stability of Echis carinatus venum protein for use in diagnostic rotational thromboelastometry," Int. J. Pharm. 495(2), pp. 692-700 (2015), 9 pages.
Erber et al., "Production and characterization of rapidly dissolving cryopellets," J. Pharm. Sci. 104, pp. 1668-1676 (2015), 9 pages.
Eriksson et al. for the BISTRO II Study Group, "A new oral direct thrombin inhibitor, dabigatran etexilate, compared with enoxaparin for prevention of thromboembolic events following total hip or knee replacement: the BISTRO II randomized trial," J. Thromb. Haemost. 3, pp. 103-111 (2005), 9 pages.
Eriksson et al. for the RECORDI Study Group, "Rivaroxaban versus enoxaparin for thromboprophylaxis after hip arthroplasty," N. Engl. J. Med. 358(26), pp. 2765-2775 (2008), 11 pages.
Eriksson et al. for the REMODEL Study Group, "Oral dabigatran etexilate vs. subcutaneous enoxaparin for the prevention of venous thromboembolism after total knee replacement: the REMODEL randomized trial," J. Thromb. Haemost. 5, pp. 2178-2185 (2007), 8 pages.
Eriksson et al. for the RE-NOVATE Study Group, "Dabigatran etexilate versus enoxaparin for prevention of venous thromboembolism after total hip replacement: a randomised, double-blind, non-inferiority trial," Lancet vol. 370, pp. 949-956 (2007), 9 pages.
Escolar et al., "Reversal of Apixaban Induced Alterations in Hemostasis by Different Coagulation Factor Concentrates: Significance of Studies In Vitro with Circulating Human Blood," PLoS One 8(11):e78696, DOI: 10.1371/journal.pone.0078696 (2013), 7 pages.
Escolar et al., "Reversal of Rivaroxaban-Induced Alterations on Hemostasis by Different Coagulation Factor Concentrates: In Vitro Studies with Steady and Circulating Human Blood," Circulation Journal vol. 79, pp. 331-338, DOI: 10.1253/circj.CJ-14-0909 (2015), 8 pages.
Feuring et al., "Lepirudin dose-dependently increases thrombelastography parameters at therapeutic plasma concentrations as measured with ROTEM®—a pilot study," Int. J. Clin. Pharmacology and Therapeutics, vol. 49, No. 10, pp. 626-628 (2011), 3 pages.
Fontana et al., "Impact of rivaroxaban on point-of-care assays," Thromb. Res. 153, pp. 65-70, (2017), 6 pages.
Friedman et al. for the RE-MOBILIZE, RE-MODEL, RE-NOVATE Steering Committees, "Dabigatran versus enoxaparin for prevention of venous thromboembolism after hip or knee arthroplasty: a pooled analysis of three trials, " Thromb. Res. 126, pp. 175-182 (2010), 8 pages.
Garcia et al., "Laboratory assessment of the anticoagulant effects of the next generation of oral anticoagulants," J. Thromb. Haemost. 11, pp. 245-252 (2013), 8 pages.
Gorlinger et al., "Fast interpretation of thromboelastometry in non-cardiac surgery: reliability in patients with hypo-, normo-, and hypercoagulability," Br J Anaesth. 110(2):222-30, DOI: 10.1093/bja/aes374 (2013), 9 pages.
Gosselin et al., "International Council for Standardization in Haematology (ICSH) recommendations for laboratory measurement of direct oral anticoagulants," Thromb. Haemost. 118, pp. 437-450 (2018), 14 pages.
Granja et al., "Multi-modal characterization of the coagulopathy associated with extracorporeal membrane oxygenation," Crit Care Med. 48(5): e400-e408, DOI: 0.1097/CCM.0000000000004286 (2020), 19 pages.

(56) References Cited

OTHER PUBLICATIONS

Gratz et al., "Protocolised thromboelastometric-guided haemostatic management in patients with traumatic brain injury: a pilot study," Anaesthesia 74, pp. 883-890 (2019), 8 pages.
Groening et al., "Coagulation management in Jersey calves: An ex vivo study," European Surgical Research 58, pp. 128-139 (2017), 12 pages.
Grottke et al., "Prothrombin complex concentrates and a specific antidote to dabigatran are effective ex-vivo in reversing the effects of dabigatran in an anticoagulation/liver trauma experimental model," Critical Care 18:R27 (2014), 10 pages.
Grottke et al., "Transient or extended reversal of apixaban anticoagulation by andexanet alfa is equally effective in a porcine polytrauma model," British J. Anaesth. 123(2), pp. 186-195 (2019),10 pages.
Haeberle et al., "Management einer komplexen Thrombozytopenie mithilfe der Thrombelastometrie [Management of complex thrombocytopenia using thromboelastometry]," Der Anaesthesist 60:1135-1140 (2011), (with English abstract), 6 pages.
Hagemo et al., "Detection of acute traumatic coagulopathy and massive transfusion requirements by means of rotational thromboelastometry: an international prospective validation study," Critital Care 19(1):97, DOI: 10.1186/s13054-015-0823-y, PMID: 25888032, PMCID: PMC4374411 (2015), 7 pages.
Harenberg et al., "Detecting anti-IIa and anti-Xa direct oral anticoagulant (DOAC) agents in urine using a DOAC dipstick," Semin. Thromb. Hemost. 45(3), pp. 275-284 (2019), 10 pages.
Havrdova et al., "Relationship of Edoxaban Plasma Concentration and Blood Coagulation in Healthy Volunteers Using Standard Laboratory Tests and Viscoelastic Analysis," J Clin Pharmacol. 61(4):522-530, DOI: 10.1002/jcph.1758, Epub Oct. 7, 2020, PMID: 33027547, (2021) 31 pages.
Hayakawa et al., "Fibrinogen level deteriorates before other routine coagulation parameters and massive transfusion in the early phase of severe trauma: a retrospective observational study," Semin. Thromb. Hemost. 41:35-42 (2015), 38 pages.
He et al., "Determination of edoxaban equivalent concentrations in human plasma by an automated anti-factor Xa chromogenic assay," Thromb. Res. 155, pp. 121-127 (2017), 7 pages.
Henskens et al., "Detecting clinically relevant rivaroxaban or dabigatran levels by routine coagulation tests or thromboelastography in a cohort of patients with atrial fibrillation," Thrombosis Journal 16:3 (2018), 7 pages.
Hermann et al., "Thrombin generation using the calibrated automated thrombinoscope to assess reversibility of dabigatran and rivaroxaban," Thromb. Haemost. 111, pp. 989-995 (2014), 7 pages.
Hirasaki et al., "Rotational Thromboelastometry for Coagulation Management During Cardiopulmonary Bypass Using Argatroban," Journal of Cardiothoracic and Vascular Anesthesia 33, pp. 1977-1982 (2019), 6 pages.
Honickel et al., "Evaluation of combined idarucizumab and prothrombin complex concentrate treatment for bleeding related to dabigatran in a lethal porcine model of double trauma," Transfusion 59, pp. 1376-1387 (2019), 12 pages.
Honickel et al., "Therapy with activated prothrombin complex concentrate is effective in reducing dabigatran-associated blood loss in a porcine polytrauma model," Thomb. And Haemost. 115.2, pp. 271-284 (2016), 14 pages.
Iapichino et al., "Point-of-Care Coagulation Tests Monitoring of Direct Oral Anticoagulants and Their Reversal Therapy: State of the Art," Thieme Medical Publishers, Inc., New York, NY, DOI: 10.1055/s-0037-1599157 (2017), 10 pages.
January et al., "2014 AHA/ ACC/HRS guideline for the management of patients with atrial fibrillation: a report of the American College of Cardiology/ American Heart Association Task Force on Practice Guidelines and the Heart Rhythm Society," J. Am. Coll. Cardiol. 64 (2014) e1-76, 69 pages.
Jourdi et al., "FXa-α2-Macroglobulin Complex Neutralizes Direct Oral Anticoagulants Targeting FXa In Vitro and In Vivo," Thromb Haemost. 118(9):1535-1544, DOI: 10.1055/s-0038-1667014, PMID: 30071567 (2018), 10 pages.
Kolde et al., "Simple and rapid method for detection and quenching of dxai effects," Thromb Res. Oct. 2012;30(Suppl 1):S181. (Abstracts and Proceedings of the 22nd International Congress on Thrombosis; Nice, France, Oct. 6-9, 2012), 1 page.
Kolde et al., "Antagonization in vitro of DXAIs and DTIs allows differentiation of NOAC effects from other hae . . . ," Hämostaseologie. Feb. 2013;33(1):A71. (Abstract; 57. Jahrestagung der Gesellschaft für Thrombose-und Hämostaseforschung (GTH), Munich, Feb. 20-23, 2013), 1 page.
Kolde et al., "Simple and rapid method for detection and quenching of dxai effects," Thromb. Res. 130, C0203, S181 (2012), 1 page.
Körber et al., "In vitro and ex vivo measurement of prophylactic dabigatran concentrations with a new ecarin-based thromboelastometry test," Transfus Med Hemother. 44(2):100-105 (2017), 6 pages.
Körber et al., "Measurement and reversal of prophylactic and therapeutic peak levels of rivaroxaban: an in vitro study," Clin Appl Thromb Hemost. 20(7):735-40, DOI: 10.1177/1076029613494468, PMID: 23832064 (2014), 6 pages.
Körber et al., "In vitro reversal of supratherapeutic rivaroxaban levels with coagulation factor concentrates," Blood Transfus. 14(5):481-6, DOI: 10.2450/2016.0205-15, PMID: 27177413, PMCID: PMC5016310 (2016), 6 pages.
Korpallova et al., "Assessing the hemostasis with thromboelastometry in direct oral anticoagulants-treated patients with atrial fibrillation," Thromb. Res. 191, pp. 38-41 (2020), 4 pages.
Korpallova et al., "Role of Thromboelastography and Rotational Thromboelastometry in the Management of Cardiovascular Diseases," Clin Appl Thromb Hemost. 24(8): 1199-1207, DOI: 10.1177/1076029618790092, PMID: 30041546; PMCID: PMC6714776 (2018), 9 pages.
Kvint et al., "Neurosurgical applications of viscoelastic hemostatic assays," Neurosurg Focus 43(5): E9, DOI: 10.3171/2017.8.FOCUS17447, PMID: 29088950 (2017), 9 pages.
Kyriakou et al., "Laboratory assessment of the anticoagulant activity of dabigatran," Clin Appl Thromb Hemost. 21(5): 434-45, DOI: 10.1177/1076029614564209, PMID: 25525048 (2015), 12 pages.
Kyriakou et al., "Laboratory Assessment of the Anticoagulant Activity of Apixaban in Patients With Nonvalvular Atrial Fibrillation," Clin Appl Thromb Hemost. 24(9_suppl): 194S-201S, DOI: 10.1177/1076029618802364, PMID: 30270642; PMCID: PMC6714834 (2018), 8 pages.
Lassen et al., "Rivaroxaban versus enoxaparin for thromboprophylaxis after total knee arthroplasty," N. Engl. J. Med. 358:2776-2786 (2008), 11 pages.
Lindhoff-Last, E., "Direct oral anticoagulants (DOAC)—Management of emergency situations: Rationale and design of the RADOA-Registry," Hamostaseologie 37, pp. 257-266 (2017), 8 pages.
Lippi et al., "Urgent monitoring of direct oral anticoagulants in patients with atrial fibrillation: a tentative approach based on routine laboratory tests," J. Thromb. Thrombolysis 38(2):269-274 (2014), 6 pages.
Mahamad et al., "Exploring the effect of favor Xa inhibitors on rotational thromboelastometry: a case series of bleeding patients," Journal of Thrombosis and Thrombolysis 47:272-279 (2019), 8 pages.
Maier et al., "Falsely Low Fibrinogen Levels in COVID-19 Patients on Direct Thrombin Inhibitors," Anesth Analg. 131(2):e117-e119, DOI: 10.1213/ANE.0000000000004949, PMID: 32371744, PMCID: PMC7219828 (2020), 3 pages.
Mani et al., "Accurate determination of rivaroxaban levels requires different calibrator sets but not addition of antithrombin," Thromb. Haemost 108:191-198 (2012), 8 pages.
Mani et al., "Measuring the anticoagulant effects of target specific oral anticoagulants—reasons, methods and current limitations," J. Thromb. Thrombolysis 36:187-194 (2013), 8 pages.
Margetić et al., "Chromogenic anti-FXa assay calibrated with low molecular weight heparin in patients treated with rivaroxaban and apixaban: possibilities and limitations," Biochem Med (Zagreb) 30(1):010702, DOI: 10.11613/BM.2020.010702, PMID: 31839722, PMCID: PMC6904970 (2020), 9 pages.

(56) References Cited

OTHER PUBLICATIONS

Martin et al., "Multimodal assessment of non-specific hemostatic agents for apixaban reversal," J Thromb Haemost. 13(3):426-36, DOI: 10.1111/jth.12830, PMID: 25630710 (2015), 11 pages.

Molinaro et al., "Low plasma fibrinogen levels with the Clauss method during anticoagulation with bivalirudin," Anesthesiology. 109(1):160-1, DOI: 10.1097/ALN.0b013e31817885b7, PMID: 18580197 (2008), 12 pages.

Mueck et al., "Clinical pharmacokinetic and pharmacodynamic profile of rivaroxaban," Clin. Pharmacokinet. 53(1):1-16 (2014), 16 pages.

Oblak et al., "Intravenous thrombolysis after idarucizumab application in acute stroke patients—a potentially increased sensitivity of thrombi to lysis?" Journal of Stroke and Cerebrovascular Diseases, vol. 28, No. 3, pp. 768-773 (2019), 6 pages.

Oswald et al., "Results of rotational thromboelastometry, coagulation activation markers and thrombin generation assays in orthopedic patients during thromboprophylaxis with rivaroxaban and enoxaparina prospective cohort study," Blood Coagulation and Fibrinolysis 26, pp. 136-144 (2015) 9 pages.

Pailleret et al., "Modified ROTEM for the detection of rivaroxaban and apixaban anticoagulant activity in whole blood," Eur. J. Anaesthesiol. 36(6), pp. 449-456 (2019), DOI: 10.1097/EJA.0000000000000903, 8 pages.

Pakraftar et al., "Dabigatran etixilate and traumatic brain injury: Evolving anticoagulants require evolving care plans," World J Clin Cases 2(8):362-6, DOI: 10.12998/wjcc.v2.i8.362, PMID: 25133148, PMCID: PMC4133427 (2014), 6 pages.

Perzborn et al., "Reversal of rivaroxaban-induced anticoagulation with prothrombin complex concentrate, activated prothrombin complex concentrate and recombinant activated factor VII in vitro," Thromb Res. 133(4):671-81, DOI: 10.1016/j.thromres.2014.01.017, PMID: 24529498 (2014), 11 pages.

Pujadas-Mestres et al., "Differential inhibitory action of apixaban on platelet and fibrin components of forming thrombi: Studies with circulating blood and in a platelet-based model of thrombin generation," PLoS One 12(2):e0171486, DOI: 10.1371/journal.pone.0171486, PMID: 28192448, PMCID: PMC5305231 (2017), 15 pages.

Salta et al., "Comparison of antithrombin-dependent and direct inhibitors of factor Xa or thrombin on the kinetics and qualitative characteristics of blood clots," Res Pract Thromb Haemost. 2(4): 696-707, DOI: 10.1002/rth2.12120, PMID: 30349889, PMCID: PMC6178701 (2018), 12 pages.

Reed et al., "Rotational thrombolelastometry produces potentially clinical useful results within 10 min in bleeding Emergency Department pateients: the DEUCE study," Eur. Journal of Emergency Med. 20(3): 160-6, DOI: 10.1097/MEJ.0b013e3283561261, 7 pages.

Samuelson et al., "Laboratory assessment of the anticoagulant activity of direct oral anticoagulants: a systematic review," Chest 151(1):127-138 (2017), 12 pages.

Schaden et al., "Ecarin modified rotational thrombelastometry: a point-of-care applicable alternative to monitor the direct thrombin inhibitor argatroban," Wien. Klin. Wochenschr. 125 (2013) 156-159, 4 pages.

Schenk et al., "Ex vivo reversal of effects of rivaroxaban evaluated using thromboelastometry and thrombin generation assay," Br. J. Anaesth. 117(4):583-591 (2016), 9 pages.

Schenk et al., "Four-factor prothrombin complex concentrate improves thrombin generation and prothrombin time in patients with bleeding complications related to rivaroxaban: a single-center pilot trial," Thromb J. 16:1, DOI: 10.1186/s12959-017-0158-9, PMID: 29344007, PMCID: PMC5763793 (2018), 10 pages.

Schmidt et al., "Reversal of apixaban induced alterations in haemostasis by different coagulation factor concentrates in patients after hip or knee replacement surgery," Blood Transfus. 17(2):157-162, DOI: 10.2450/2018.0028-18, PMID: 29757137, PMCID: PMC6476738 (2019), 6 pages.

Schmidt et al., "Relative effects of plasma, fibrinogen concentrate, and factor XIII on ROTEM coagulation profiles in an in vitro model of massive transfusion in trauma," Scand. J. Clin. Lab. Invest. 77:6, pp. 397-405 (2017), 10 pages.

Schocl et al., "FIBTEM provides early prediction of massive transfusion in trauma," Crit Care 15(6):R265, DOI: 10.1186/cc10539, PMID: 22078266, PMCID: PMC3388656 (2011), 11 pages.

Schoergenhofer et al., "The use of frozen plasma samples in thromboelastometry," Clin Exp Med. 17(4):489-497, DOI: 10.1007/s10238-017-0454-5, PMID: 28210886, PMCID: PMC5653723 (2017), 9 pages.

Schultz et al., "The reversal effect of prothrombin complex concentrate (PCC), activated PCC and recombinant activated factor VII against anticoagulation of Xa inhibitor," Thromb J. 15:6, DOI: 10.1186/s12959-017-0129-1, PMID: 28239301, PMCID: PMC5319105 (2017), 8 pages.

Schultz et al., "The reversal effect of prothrombin complex concentrate (PCC), activated PCC and recombinant activated factor VII in apixaban-treated patients in vitro," Res Pract Thromb Haemost. 1(1):49-56, DOI: 10.1002/rth2.12015, PMID: 30046673, PMCID: PMC6058213 (2017), 8 pages.

Schultz et al., "Activated prothrombin complex concentrate to reverse the factor Xa inhibitor (apixaban) effect before emergency surgery: a case series," J Med Case Rep. 12(1):138, DOI: 10.1186/s13256-018-1660-9, PMID: 29764497, PMCID: PMC5954448 (2018), 5 pages.

Seyve et al., "Impact of four direct oral anticoagulants on rotational thromboelastometry (ROTEM)," Int. J. Lab. Hematol. 40:84-93 (2018), 10 pages.

Solbeck et al., "The anticoagulant effect of therapeutic levels of dabigatran in atrial fibrillation evaluated by thrombelastography (TEG), Hemoclot Thrombin Inhibitor (HTI) assay and Ecarin Clotting Time (ECT)," Scand. J. Clin. Lab. Invest. vol. 78, No. 1-2, pp. 25-30 (2018), 6 pages.

Sorensen et al., "Whole blood coagulation thrombelastographic profiles employing minimal tissue factor activation," J. Thromb. Haemost. 1(3):551-558 (2003), 8 pages.

Stein et al., "Dabigatran anticoagulation and Stanford type A aortic dissection: lethal coincidence," Acta Anaesthesiol. Scand. 58:630-637 (2014), 7 pages.

Stephenne et al., "Bivalirudin in combination with heparin to control mesenchymal cell procoagulant activity," PLoS One 7(8):e42819, DOI: 10.1371/journal.pone.0042819, PMID: 22900053, PMCID: PMC3416788 (2012), 13 pages.

Sucker et al., "Rotational thrombelastometry for the bedside monitoring of recombinant hirudin," Acta Anaesthesiol. Scand. 52:358-362 (2008), 5 pages.

Takeshita et al., "Whole Blood Point-of-Care Testing for Incomplete Reversal with Idarucizumab in Supratherapeutic Dabigatran," Anesth Analg. 130(2):535-541, DOI: 10.1213/ANE.0000000000004419, PMID: 31490820 (2020), 7 pages.

Taune et al., "Rapid determination of anticoagulating effects of dabigatran in whole blood with rotational thromboelastometry and a thrombin-based trigger," J. Thromb. Haemost. 16:2462-2470 (2018), DOI: 10.1111 /jth.14308, 9 pages.

Taune et al., "Whole blood coagulation assays ROTEM and T-TAS to monitor dabigatran treatment," Thromb. Res. 153:76-82 (2017), 7 pages.

Teruya et al., "Monitoring bivalirudin therapy in children on extracorporeal circulatory support devices: Thromboelastometry versus routine coagulation testing," Thromb. Res. 186:54-57 (2020), 4 pages.

Thorberg et al., Reversal by the specific antidote, idarucizumab, of elevated dabigatran exposure in a patient DOI: 10.1093/bja/aew244 (2016), 3 pages.

Tripodi et al., "Position paper on laboratory testing for patients on direct oral anticoagulants. A consensus document from the SISET, FCSA, SIBioC and SIPMeL," Blood Transfus. 16:462-470 (2018), 9 pages.

(56) References Cited

OTHER PUBLICATIONS

Tsantes et al., "Comparative assessment of the anticoagulant activity of rivaroxaban and dabigatran in patients with nonvalvular atrial fibrillation: a nonintentional study," Medicine (Baltimore) 95(14):e3037 (2016), 6 pages.
Tsantes et al., "Impact of dabigatran on platelet function and fibrinolysis," J. Neurological Sciences 357:204-208 (2015), 5 pages.
Van Ryn et al., "Measurement of Dabigatran in Standardly Used Clinical Assays, Whole Blood Viscoelastic Coagulation, and Thrombin Generation Assays," Clin Lab Med 34:479-501 (2014), 23 pages.
Vedovati et al., "Global thromboelastometry in patients receiving direct oral anticoagulants: the RO-DOA study," J Thromb Thrombolysis. 49(2):251-258 (2020), 8 pages.
Vedovati et al., "Thromboelastometry to Detect Anticoagulant Effect of Apixaban in Patients with Non Valvular Atrial Fibrillation," Res. & Prac. In Thromb. & Haemost., ISTH-Wiley, PB423, pp. 500-501 (2017), 2 pages.
Whiting et al., "TEG and ROTEM: technology and clinical applications," Am. J. Hematol. 89(2):228-232 (2014), 5 pages.
Wild et al., "Diffuse bleeding after multiple trauma in a patient treated with Dabigatran," European Journal of Anesthesiology 30:98 (2013), 1 page.
Young et al., "Thrombin generation and whole blood viscoelastic assays in the management of hemophilia: current state of art and future perspectives," Blood 121(11):1944-1950 (2013), 12 pages.
Extended European Search Report for European patent application No. 21198139.4, dated Feb. 21, 2022, (11 pages).
Schäfer, Simon Thomas et al: "Real-time detection and differentiation of direct oral anticoagulants (rivaroxaban and dabigatran) using modified thromboelastometric reagents", Thrombosis Research, vol. 190, Apr. 18, 2020 (Apr. 18, 2020), pp. 103-111, XP055886765, Amsterdam, NL. ISSN: 0049-3848, DOI: 10.1016/j.thromres.2020.04.019, (9 pages).
Grone, P. et al: "Differenzierung verschiedener Antikoagulanzien mittels modifizierter Thromboelastometrie-ein Entscheidungsalgorithmus", 34. Wissenschaftliche Arbeitstage Der Dgai, Aug. 1, 2020 (Aug. 1, 2020), pp. 1-27, XP055887123, (1 page).
Schäfer, S et al: "Differenzierung verschiedener Antikoagulanzien mittels modifizierter Thromboelastometrie-ein Entscheidungsalgorithmus", Anasthesiologie & Intensivmedizin, vol. 61, May 1, 2020 (May 1, 2020), pp. 1-103, XP055887198, Retrieved from the Internet: URL:https://www.ai-online.info/images/ai-ausgabe/2020/05-2020/Supplement_11-2020_DAC_Abstracts.pdf, (1 page).
Dias, João D. et al: "Rapid point-of-care detection and classification of direct-acting oral anticoagulants with the TEG 6s: Implications for trauma and acute care surgery", Journal of Trauma and Acute Care Surgery, vol. 87, No. 2, Aug. 1, 2019 (Aug. 1, 2019), pp. 364-370, XP055886986, US ISSN: 2163-0755, DOI: 10.1097ff A.0000000000002357 Retrieved from the Internet: URL:http://dx.doi.org/10.1097ff A.0000000000002357; (7 pages).
Schäfer, Simon Thomas et al: "Point-of-care detection and differentiation of anticoagulant therapy—development of thromboelastometry-guided decision-making support algorithms", Thrombosis Journal, vol. 19, No. 1, Sep. 7, 2021 (Sep. 7, 2021), XP055886753, DOI: 10.1186/s12959-021-00313-7 Retrieved from the Internet: URL:https://www.ncbi.nlm.nih.gov/pmc/articles/PMC8425056/pdf/12959_2021_Article_313.pdf; (11 pages).
Anonymous: "Decision tree learning—Wikipedia", Sep. 9, 2020 (Sep. 9, 2020), XP055887452, Retrieved from the Internet: URL:https://en.wikipedia.org/w/index.php?title=Decision_tree_learning&oldid=97753596 [retrieved on Feb. 4, 2022], (10 pages).
Calatzis et al., "Prothrombinase-Induced Clotting Time Assay for Determination of the Anticoagulant Effects of Unfractionated and Low-Molecular-Weight Heparins, Fondaparinux, and Thrombin Inhibitors," Am. J. Clin. Pathol. 130:446-454 (2008), 10 pages.
Harenberg et al., "Determination of Dabigatran in Human Plasma Samples," Semin. Thromb. Hemost. 38:16-22 (2012), 7 pages.
Konkle, B., "Monitoring target specific anticoagulants," J. Thromb. Thrombolysis 35:387- 390 (2013), 5 pages.
Funk, D., "Coagulation Assays and Anticoagulant Monitoring," Hematology Am Soc Hematol Educ Program 2012(1): 460-465 (2012), 6 pages.
Eriksson et al., "Comparative Pharmacodynamics and Pharmacokinetics of Oral Direct Thrombin and Factor Xa Inhibitors in Development," Clin Parmacokinet 48:1-22 (2009), 22 pages.
"Search Report: Prior Art to [Redacted]," Global Prior Art Inc., Boston, MA, Apr. 22, 2020, 2 pages.
"Search Report: Freedom-to-Operate Search Surrounding DOAC Assay Cartridges as Outlinedin Client-Provided '2018-08-09 DOAC overview," Global Prior Art Inc., Boston, MA, Apr. 27, 2020, 3 pages.
Fareed et al., "Preclinical Studies on a Low Molecular Weight Heparin," Thromb. Res. 81(2S): S1-S27 (1996), 27 pages.
Paccaly et al., "Pharmacodynamic markers in the early clinical assessment of otamixaban, a direct factor Xa inhibitor," Thromb. Haemost. 94:1156-1163 (2005), 8 pages.
Ortel, T., "Laboratory Diagnosis of the Lupus Anticoagulant," Curr. Rheumatol. Rep. 14:64-70 (2011), 7 pages.
Baruch, L., "Laboratory Monitoring of Anticoagulant Medications: Focus on Novel Oral Anticoagulants," Postgrad. Med. 125:135-145 (2013), 11 pages.

\* cited by examiner

DETECTING AND MONITORING ORAL ANTICOAGULANTS OR INTRAVENOUS DIRECT THROMBIN INHIBITORS IN A BLOOD SAMPLE

CROSS-REFERENCE TO RELATED APPLICATIONS

Priority is hereby claimed to U.S. Provisional Application No. 63/080,944 filed on Sep. 21, 2020 and to U.S. Provisional Application No. 63/091,018 filed on Oct. 13, 2020. U.S. Provisional Application No. 63/080,944 and U.S. Provisional Application No. 63/091,018 are incorporated herein by reference.

TECHNICAL FIELD

This specification relates generally to systems and processes for detecting and monitoring oral anticoagulants or intravenous direct thrombin inhibitors in a blood sample.

BACKGROUND

Vitamin K-antagonists (VKAs), direct oral anticoagulants (DOACs), and intravenous direct thrombin inhibitors (IV-DTIs) directly inhibit the blood's ability to form blood clots. Oral anticoagulants (VKAs and DOACs) include anticoagulants for the prevention and therapy of thromboembolic events. Taking VKAs, DOACs and IV-DTIs can increase a patient's risk of bleeding, particularly after trauma, during surgery, and during invasive interventions. In order to treat the patient, it may therefore be necessary to determine whether the patient is using a VKA, DOAC or an IV-DTI. Particularly in emergency situations, the time to perform testing needed to detect and/or to monitor the effects of a VKA, a DOAC, or an IV-DTI should be short.

SUMMARY

An example method for detecting a presence of one or more oral anticoagulants or intravenous (IV) direct thrombin inhibitors in a blood sample may include the following operations: receiving parameters that are based on viscoelastic tests; comparing the parameters to predefined threshold values, where the parameters and the predefined threshold values are based on an identity of the one or more oral anticoagulants or the IV direct thrombin inhibitors; and detecting, based on the comparing, the presence of the one or more oral anticoagulants or IV direct thrombin inhibitors in the blood sample. The viscoelastic tests are performed on portions of the blood sample to obtain the parameters. The viscoelastic tests include both a viscoelastic test based on Ecarin activation and a viscoelastic test with low tissue factor activation. The example method may include one or more of the following features, either alone or in combination.

Examples of parameters that may be received by the method include parameters relating to the time that it takes for clotting to occur and clot firmness.

Detecting the presence of the one or more oral anticoagulants or intravenous (IV) direct thrombin inhibitors in a blood sample may include detecting a type of the anticoagulant or IV direct thrombin inhibitor or an amount of the anticoagulant or IV direct thrombin inhibitor. Detecting the presence of the one or more oral anticoagulants or intravenous (IV) direct thrombin inhibitors may also include, or be part of processes for, monitoring or differentiating among anticoagulants or IV direct thrombin inhibitors.

The one or more oral anticoagulants may include a direct factor Xa inhibitor, and detecting may include detecting the direct factor Xa inhibitor. The one or more oral anticoagulants may include a vitamin K-antagonist, and detecting may include detecting the vitamin K-antagonist. Detecting may include determining that the blood sample has been subjected to hemodilution. Detecting hemodilution may include comparing parameters to thresholds to differentiate hemodilution from anticoagulants in the blood.

Detecting the presence of the one or more oral anticoagulants or IV direct thrombin inhibitors in the blood sample may include performing a receiver operating characteristic (ROC) curve analyses based on the parameters. Detecting the presence of the one or more oral anticoagulants or IV direct thrombin inhibitors in the blood sample may include performing a decision tree analysis based on the parameters. The decision tree analysis may be performed using a decision tree. The decision tree may be based, at least in part, on the parameters and on combinations of the parameters. For example, the decision tree analysis may include traversing multiple nodes to reach a destination at which a detection result is determined where, at at least some of the nodes, a parameter is compared to a threshold and, based on the comparison, one of multiple different branches is followed on the way to the destination. The combinations of the parameters may be user-provided. For example, a computing system that performs the method may provide the user with a prompt and receive input from the user via a device such as mouse, touch-screen, or the like. The decision tree may be generated using machine learning. For example, a computing system may receive training data and implement machine learning processes to construct a decision tree that produces results consistent with the training data. The decision tree may later be validated using a different set of validation data. In some implementations, the decision trees can be pre-structured, e.g., in terms of layers and/or operation sequences, and parameterized using the training data. The decision tree may include multiple levels. A number of the multiple levels may be generated automatically based on external input.

The operations may include generating data for a user interface to display detected oral anticoagulants or IV direct thrombin inhibitors. The viscoelastic tests may be performed using a cartridge having multiple chambers. Each of the portions of the blood sample may be received in one of the multiple chambers. Each of the multiple chambers may be for performing a viscoelastic test on a corresponding portion of the blood sample.

The parameters may have been determined experimentally to enable differentiation at greater than a predetermined level of accuracy. The predetermined level of accuracy may be at least 70%.

Also described herein is an example system for detecting a presence of one or more oral anticoagulants or IV direct thrombin inhibitors in a blood sample. The system includes one or more processing devices and non-transitory machine-readable storage storing instructions that are executable by the one or more processing devices to perform the operations described above in the method. The system may include any features described herein with respect to the method.

Any two or more of the features described in this specification, including in this summary section, can be combined to form implementations not specifically described herein.

The systems, processes, components, structures, and variations thereof described herein, or portions thereof, can be implemented using, or controlled by, a computer program product that includes instructions that are stored on one or more non-transitory machine-readable storage media, and that are executable on one or more processing devices to execute at least some of the operations described herein. The systems, processes, components, structures, and variations thereof described herein, or portions thereof, can be implemented as an apparatus, method, or electronic systems that can include one or more processing devices and memory to store executable instructions to implement the various operations. The systems, processes, components, structures, and variations thereof described herein may be configured, for example, through design, construction, arrangement, placement, programming, operation, activation, deactivation, and/or control.

The details of one or more implementations are set forth in the accompanying drawings and the description below. Other features, objects, and advantages will be apparent from the description and drawings, and from the claims.

DESCRIPTION OF THE DRAWINGS

Like reference numerals in different figures indicate like elements.

DETAILED DESCRIPTION

Figure 1:
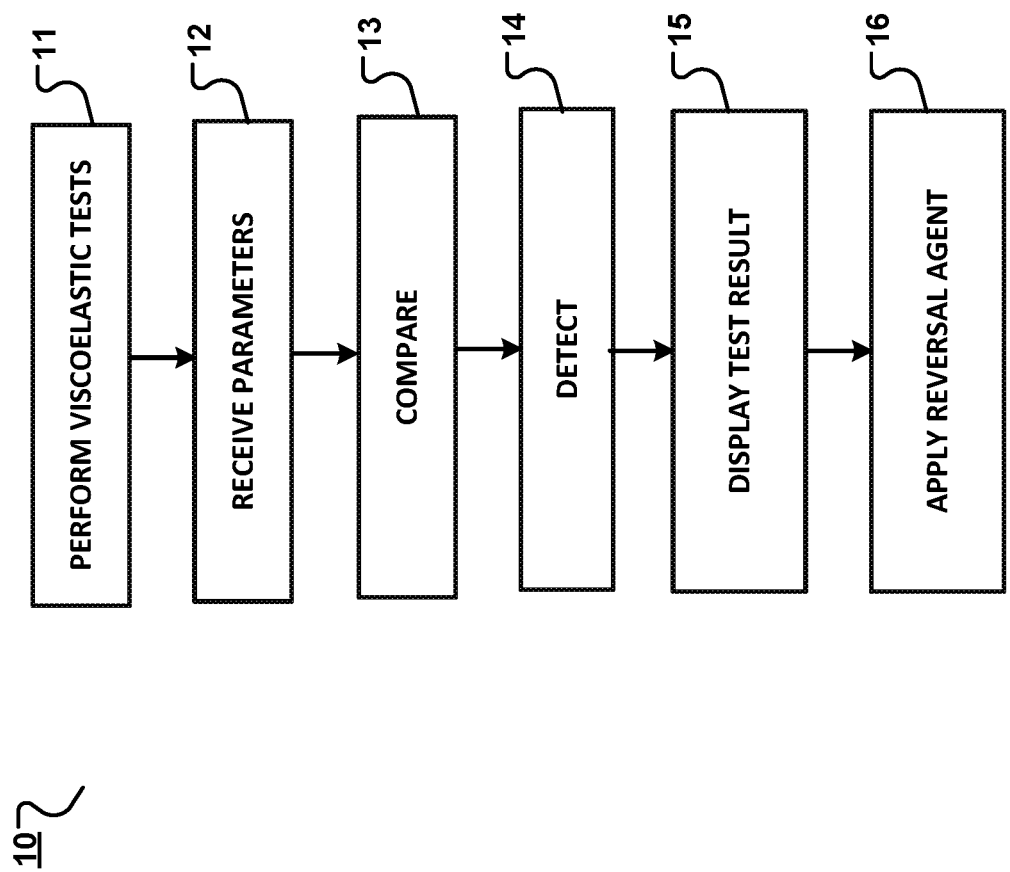
FIG. 1 is a flowchart showing operations included in an example process for detecting, differentiating, and monitoring oral anticoagulants, intravenous direct thrombin inhibitors (IV DTIs), and coagulopathies in a blood sample.

Various types of anticoagulants, including direct oral anticoagulants (DOACs), vitamin K antagonists (VKA), and intravenous direct thrombin inhibitors (IV-DTIs) are used for prevention and therapy of thromboembolic events. In emergencies, such as stroke or acute bleeding, medical personnel benefit from accurate and rapid tests to determine whether a patient has one or more types of anticoagulants, e.g., VKAs, DOACs, or IV-DTIs, in the their blood and possibly what exact anticoagulant class is present within the determined type, especially if the patient is unconscious or disoriented and the patient's drug history is not available. It may be necessary to differentiate among DOACs, IV-DTIs, and VKAs, and also to differentiate direct factor Xa inhibitors (DXaIs), DTIs, and VKAs from dilutional coagulopathy (DIL).

DXAIs and oral DTIs are called DOACs since they block factor Xa or factor IIa (=thrombin) directly without the intermediation of antithrombin. In contrast, heparinoids (unfractionated heparin (UFH)) or low molecular weight heparin (LMWH)) work indirectly by amplifying the effect of antithrombin. Therefore, they are called indirect Xa and thrombin inhibitors. VKAs and DOACs together are called oral anticoagulants (OACs). It may be important to detect and differentiate the OACs in an emergency situation because of the need to implement different therapeutic interventions in case of bleeding. For example, VKAs may be treated with prothrombin complex concentrate or fresh frozen plasma. DXaIs can be reversed by andexanet alfa (an antidote specific for DXaIs), Dabigatran—which is an oral DTI—can be reversed by idarucizumab (PRAXBIND®), which is an antibody for dabigatranand and therefore neutralizes this specific drug. The dilutional coagulopathy (DIL) called hemodilution can be treated by fibrinogen replacement using givibf fibrinogen concentrate.

Regarding DTIs, dabigatran (an oral DTI) is given orally for thrombosis prophylaxis or to treat thrombosis in ambulant or hospitalized patients, and argatroban or bivalirudin (IV DTIs) are given via continuous intravenous infusion to critically ill patients at the intensive care unit (argatroban or bivalirudin). The latter are not given to ambulant patients. Therefore, in some examples, IV DTIs are monitored for their effects (used for anticoagulation in critically ill patients) and subsequent dose adjustment.

Accordingly, herein are examples of systems and processes (referred to as "the processes") for detecting the presence of one or more types of anticoagulants, including VKAs, DXaIs, and DTIs, in a blood sample. In some examples, the presence of specific types of anticoagulants (VKAs, DXaIs, and DTIs) can be detected and monitored. In some examples, to differentiate among anticoagulants, the mode of action (VKA, DXaI or DTI) is used but not the application route (oral or IV). Therefore, in some examples, the processes differentiate among VKA, DXaIs and DTI. Whether an oral DTI (e.g., dabigatran) or an IV DTI (e.g., argatroban or bivalirudin) is used is dependent on the patient population (ambulant/outpatient: oral; critically ill patient on the ICU: IV).

Examples of exact (or specific) anticoagulants that may be detected and identified by the processes include, but are not limited to, oral DTI (e.g., dabigatran), IV-DTIs (e.g., argatroban and bivalirudin), DXaIs (e.g., rivaroxaban, apixaban, or edoxaban), and vitamin K antagonists (VKAs) (e.g., phenprocoumon or warfarin). The processes may also be used for detecting, based on a patient's blood sample, the presence of a dilutional coagulopathy (DILs), such as hemodilution, due to crystalloid or colloid infusion. The processes may be performed on a machine operated by a clinician at a point-of-care (POC) facility, such as an emergency room, operating room, intensive care unit, or an urgent care facility or in a laboratory. The machine may be a fully automated viscoelastic testing device, such as but not limited to a ROTEM® device, that performs a viscoelastic testing process. Viscoelastic tests measure viscoelastic properties of a blood sample, e.g., in the presence of one or more reagents, in order to assess coagulation of the blood sample. Alternatively, the machine may include a processor that receives viscoelastic testing results, regardless of whether such viscoelastic tests are manual, semi-manual, or automated, and process the testing results to perform the processes described herein.

FIG. 1 shows an example implementation of operations 10 performed in a process of the foregoing type. Process 10 includes performing (11) viscoelastic tests on portions a blood sample to obtain parameters of the type described below. Examples of viscoelastic tests that may be used with the processes include the following.

A first viscoelastic test—referred to generally as "TEST ONE"—is used to monitor the blood coagulation process of citrated whole blood samples after activating the extrinsic pathway, blocking platelet contribution to clot firmness, and eliminating a heparin-like effect. Examples of such a test include the ROTEM® assay FIBTEM, the CLOTPRO® assay FIBtest, and the TEG® assay Functional Fibrinogen. The reagent for the FIBTEM assay includes cytochalasin D to eliminate the platelet contribution to clot firmness. FIBTEM clotting characteristics are described by the ROTEM® parameters for clotting time CT (corresponding to the TEG® parameter reaction(r)-time) and clot firmness parameters. The clot firmness parameters include amplitude of clot firmness 5, 10, 15 or 20 minutes after CT (A5, A10, A15, A20) or maximum clot firmness MCF (corresponding to the TEG® parameter maximum amplitude (MA)).

Based on TEST ONE's usefulness in detecting hypofibrinogenemia and in predicting bleeding and transfusion, TEST ONE parameters may be used in the processes for detection of dilutional coagulopathy and/or for differentiation between the presence of an oral anticoagulant or IV-DTI. Furthermore, TEST ONE provides reliable clot firmness results even at oral and IV DTI concentrations that significantly impact conventional plasma fibrinogen determinations. Therefore, TEST ONE parameters may be particularly useful for patients suspected to have been treated with DTIs.

A second viscoelastic test—referred to generally as "TEST TWO"—is used to monitor the blood coagulation process after activation with a low tissue factor concentration via the extrinsic pathway in citrated whole blood samples and eliminating a potential heparin-like effect. Low tissue factor activation increases sensitivity to minor changes in thrombin generation and, therefore, enables detecting anticoagulants with minor effects on clotting times such as, but not limited to, apixaban. An example of such a test is the ROTEM® assay TFTEM. The reagent for TFTEM includes a reduced tissue factor concentration for reduced activation of the extrinsic pathway, which increases the sensitivity of TFTEM to mild anticoagulant effects. TFTEM clotting characteristics are described by the ROTEM® parameters CT and clot firmness parameters A5, A10, A15, A20, and MCF. TFTEM may be modified by the addition of pegylated, activated factor X (PEG-Xa=factor Xa-inhibitor-catcher). PEG-Xa is a factor-Xa molecule modified by polyethylene glycol (PEG) coupled to lysine residues. The modification of the factor-Xa molecule with PEG prevents an interaction of factor-Xa with other macromolecules such as prothrombin, but the PEG-Xa molecule binds DXaIs, e.g., rivaroxaban, apixaban and edoxaban, at its active center.

A third viscoelastic test—referred to generally as "TEST THREE"—is used to monitor the blood coagulation process via activation by the snake venom Ecarin. Examples of such a test include the ROTEM® assay ECATEM and the CLOTPRO® assay ECAtest. The reagent for the ECATEM test includes Ecarin as an activator. Ecarin directly converts prothrombin to meizothrombin, which has a lower activity compared to thrombin and which is inhibited by direct thrombin inhibitors such as hirudin, argatroban, bivalirudin, and dabigatran, but not by heparin. ECATEM may be modified by the addition of pegylated, activated factor IIa (PEG-IIa=factor IIa-inhibitor-catcher). ECATEM is insensitive to changes in the activity of factors V, VII, VIII, IX, X, XI, or XII, and thus might be unaltered with DXaIs but sensitive to DTIs. PEG-IIa is a thrombin molecule modified by PEG coupled to lysine residues. The modification of thrombin with PEG prevents an interaction of thrombin with other macromolecules such as fibrinogen, but the thrombin molecule can still bind DTIs at its active center. PEG-IIa can be used to detect all DTIs, whether oral (dabigatran) or IV (argatroban or bivalirudin), whereas the clinically used antidote idarucizumab (PRAXBIND®) only neutralizes the effect of dabigatran since it is a specific antibody for dabigatran. ECATEM clotting characteristics are described by the ROTEM® parameters CT and the clot firmness parameters A5, A10, A15, A20, and MCF.

A fourth viscoelastic test—referred to generally as "TEST FOUR"—is used to monitor the blood coagulation process via the intrinsic pathway in citrated whole blood samples and eliminates a potential heparin-like effect. Examples of such a test include the ROTEM® assay HEPTEM, the CLOTPRO® assay HEPtest, and the TEG® assay heparinase kaolin-TEG. The reagent for the HEPTEM assay includes calcium chloride, ellagic acid as an activator of the intrinsic pathway, and heparinase to neutralize a potential heparin effect. HEPTEM clotting characteristics are described by ROTEM® parameter CT and clot firmness parameters A5, A10, A15, A20, and MCF. Using TEST FOUR parameters in the processes may improve differentiation of VKAs relative to DXaIs.

Alternatively or in addition, a test activating the blood coagulation process via the extrinsic pathway by high tissue factor concentrations in citrated whole blood samples and eliminating a potential heparin-like effect, but not eliminating platelet contribution to clot firmness, can be used as TEST FOUR or as a fifth test (referred to generally as "TEST FIVE"). Examples of such a test include the ROTEM® assay EXTEM, the CLOTPRO® assay EXtest, and the TEG® assay rapid-TEG. The reagent for the EXTEM assay includes calcium chloride for recalcification of the citrated blood sample, tissue factor as an activator of the extrinsic pathway, and polybrene as a heparin inhibitor. EXTEM clotting characteristics are described by CT and clot firmness parameters A5, A10, A15, A20, and MCF. TEST FIVE parameters may be used to assess the effect of VKAs, and high blood concentrations of DXaIs and DTIs.

The processes receive the test parameters ("parameters") obtained from two or more of the foregoing tests and use them to detect, to differentiate, and to monitor the presence and effects of different types of anticoagulants, including VKAs, DXaIs, DTIs, and DIL, in a blood sample. The parameters received from the tests may be modified and may be compared to threshold values to determine the presence and identities of the VKAs, DXaIs, DTIs, and DILs. As shown in FIG. 1, example process 10 receives (12) the parameters and compares (13) the parameters to predefined thresholds in order to rule-in or to rule-out anticoagulants or coagulopathies in the blood sample. The comparisons may be implemented using decision tree and/or receiver operating characteristic (ROC) analyses such as those described below.

A decision tree can be represented as a tree diagram for the purpose of user visualization. The decision tree can be implemented using software module(s) that when executed, perform the processes to detect, to differentiate, and to monitor anticoagulants and coagulopathies. ROC curve analyses may be used to implement decisions represented by nodes of the decision tree. A ROC curve is a plot of a true positive rate (sensitivity (SE)) as a function of false positive rate (100−specificity) for different cut-off points of a parameter. Each point on the ROC curve represents a sensitivity/specificity pair corresponding to a particular decision threshold. The area under the ROC curve (AUC) is a measure of how well a parameter can distinguish between two substances or clinical outcomes. Since a single ROC curve analysis can only answer a yes or no question, multiple ROC curve analyses may be used or needed to implement a decision tree.

Example parameters used in the decision trees include the time (referred to generally as "TIME") it takes for clotting to occur for a given test, such as TEST ONE. An example of this parameter is CT for a ROTEM® viscoelastic test. Example parameters used in the decision trees also relate to clot firmness (referred to generally as "FIRM"). An example of this parameter is clot amplitude (A) in a ROTEM® viscoelastic test. In the descriptions below, the parameter subscript refers to the test. So, for example, $TIME_{TEST\_ONE}$ refers to the time it takes for blood to clot using TEST ONE, and $FIRM_{TEST\_TWO}$ refers to the firmness of the clot produced using TEST TWO after a predetermined time, such as five minutes after CT, ten minutes after CT, and so forth. The parameters to be used in the decision tree nodes may be determined through experimentation and those parameters may be input to the processes. For example, the parameters, or combinations thereof, may be input to a computer-implemented machine learning process to generate the decision tree. In another example, the parameters, or combinations thereof, may be used by an investigator implementing the processes using ROC curve analyses.

The parameters used in the decision tree analyses may also include combinations of the above parameters through multiplication, division, addition or subtraction, for example to produce values that are usable to differentiate anticoagulants and coagulopathies. These combinations and values have been determined experimentally external to the processes. These values may also be scaled to implement comparisons to the threshold values described below.

The following one or more parameters and combinations of parameters can enable detection and differentiation between (i) an oral anticoagulant and (ii) hemodilution or no coagulopathy: $TIME_{TEST\_TWO}$ (e.g., $CT_{TFTEM}$), the product of $TIME_{TEST\_TWO}$ and $FIRM_{TEST\_TWO}$ (e.g., ($CT_{TFTEM} \times A5_{TFTEM}$)/100), and the product $TIME_{TEST\_TWO}$ and $TIME_{TEST\_FOUR}$ (e.g., ($CT_{TFTEM} \times CT_{HEPTEM}$)/1000). The following one or more parameters and combination of parameters can enable detection and differentiation between (i) hemodilution and (ii) no coagulopathy: $FIRM_{TEST\_FIVE}$ (e.g., $A5_{EXTEM}$), $FIRM_{TEST\_ONE}$ (e.g., $A5_{FIBTEM}$), and the product of $TIME_{TEST\_TWO}$ and $FIRM_{TEST\_ONE}$ (e.g., ($CT_{TFTEM} \times A5_{FIBTEM}$)/100). The following one or more parameters and combination of parameters can enable detection and differentiation between (i) DXaIs and (ii) DTIs and VKAs: $TIME_{TEST\_TWO}$ (e.g., $CT_{TFTEM}$), and the quotient of $TIME_{TEST\_TWO}$ and $TIME_{TEST\_THREE}$ (e.g., $CT_{TFTEM}/CT_{ECATEM}$). The following parameter can enable detection and differentiation between (i) DTIs and (ii) DXaIs and VKAs: $TIME_{TEST\_THREE}$ (e.g., $CT_{ECATEM}$). The following one or more parameters and combinations of parameters can enable detection and differentiation between (i) DTIs and (ii) VKAs: $TIME_{TEST\_THREE}$ (e.g., $CT_{ECATEM}$) and the product of $TIME_{TEST\_THREE}$ and $TIME_{TEST\_FOUR}$ (e.g., ($CT_{ECATEM} \times CT_{HEPTEM}$)/1000). The following one or more parameters and combination of parameters can enable detection and differentiation between (i) DTIs and (ii) DXaIs: $TIME_{TEST\_THREE}$ (e.g., $CT_{ECATEM}$), and the quotient of $TIME_{TEST\_TWO}$ and $TIME_{TEST\_THREE}$ (e.g., $CT_{TFTEM}/CT_{ECATEM}$). The following one or more parameters and combination of parameters can enable detection and differentiation between (i) DXaIs and (ii) VKAs: $TIME_{TEST\_TWO}$ (e.g., $CT_{TFTEM}$), and the quotient of $TIME_{TEST\_TWO}$ and $TIME_{TEST\_THREE}$ (e.g., $CT_{TFTEM}/CT_{ECATEM}$). Use of these parameters in a decision tree analysis enables the identification of different oral anticoagulants (e.g., VKAs, DXaIs, and DTIs) and IV DTIs and enables their differentiation from a dilutional coagulopathy (DIL) and the absence of (that is, no) coagulopathy. However, use of the parameters is not limited to any particular form of a decision tree. For example, different numbers of the parameters and/or combinations of parameters can be selected for use. The parameters or combinations of parameters can be used in different sequences and/or at different locations of decision trees having different structures or number of layers. Different scaling or constants can be used to modify the parameters or combinations of parameters.

The threshold values used in the comparisons can be determined automatically by the machine learning process or manually, e.g., through experiments. In some implementations, the threshold values can change based on the amount of data available for training the decision tree. As the available data increases, the decision trees can be modified/improved by using updated threshold values for improved precision. As described previously, the values for the selected parameters and combinations of parameters can be obtained directly or indirectly calculated from viscoelastic testing results. The threshold values may also change when additional, new, or different DOACs and/or IV DTIs are used in the system.

In some implementations, the parameters and the combinations of parameters used in the decision tree analyses have been determined experimentally to enable detection and differentiation based thereon with at least with an accuracy of 70%. For example, for node 91 of FIG. 4, a comparison resulting in $TIME_{TEST\_ONE}$ having a value greater than threshold ("T") T16 has been proven, e.g., through validation data, to produce an accurate differentiation of DXaI at least 70% of the time. In some implementations, the parameters and the combinations of parameters used in the decision tree may have been determined experimentally to enable their respective differentiations with an accuracy of greater than 70%—for example, 75%, 80%, 85%, and so forth.

Figure 2:
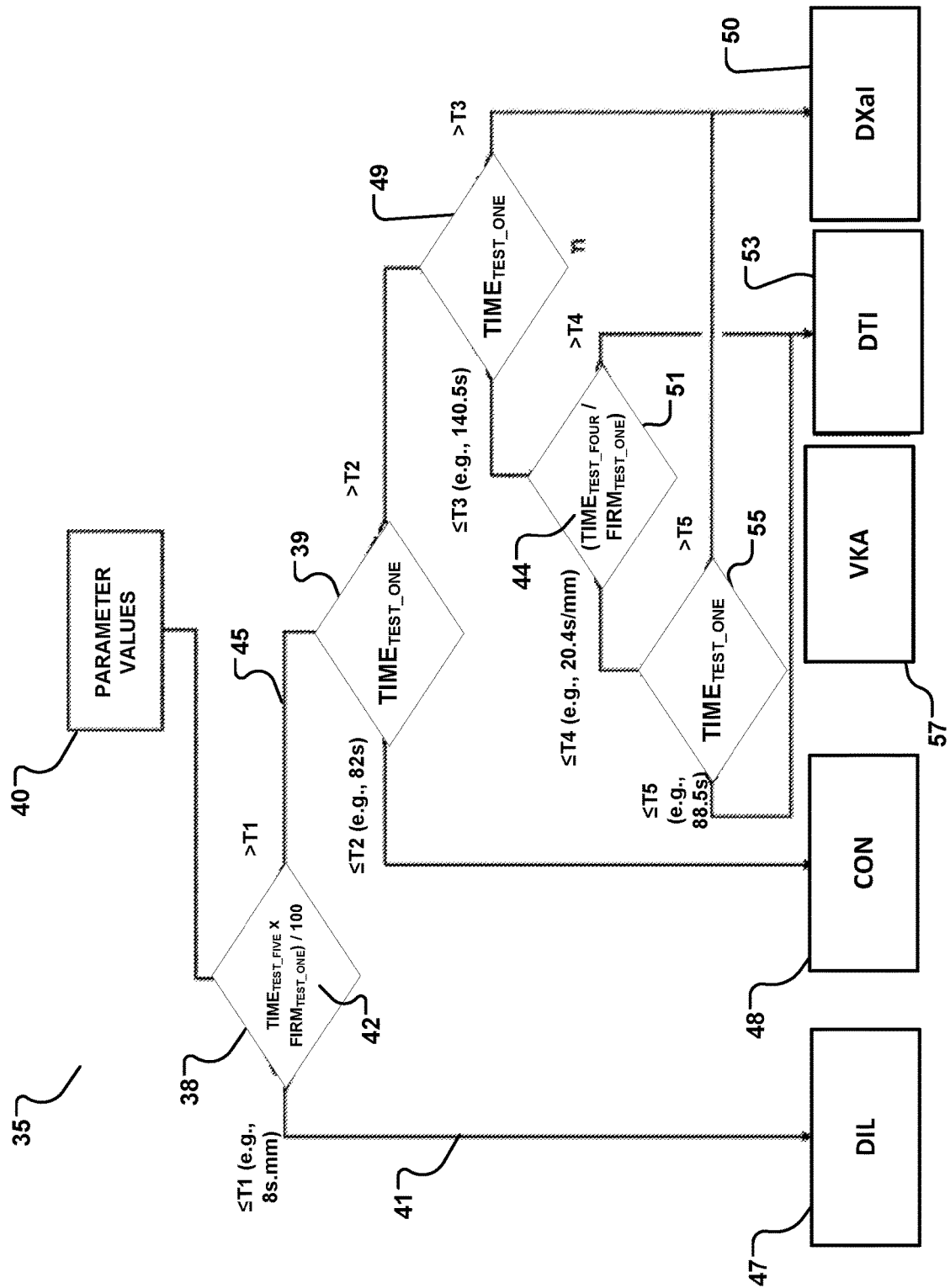
FIG. 2 is an example of a decision tree that is usable to implement comparisons used to differentiate among oral anticoagulants (such as vitamin K antagonists (VKA), direct factor Xa inhibitors (DXaIs) and oral DTIs), IV DTIs, and/or coagulopathies and, possibly, to determine the presence of a particular anticoagulant class (VKA, DXaI, or DTI) in a blood sample.
Figure 3:
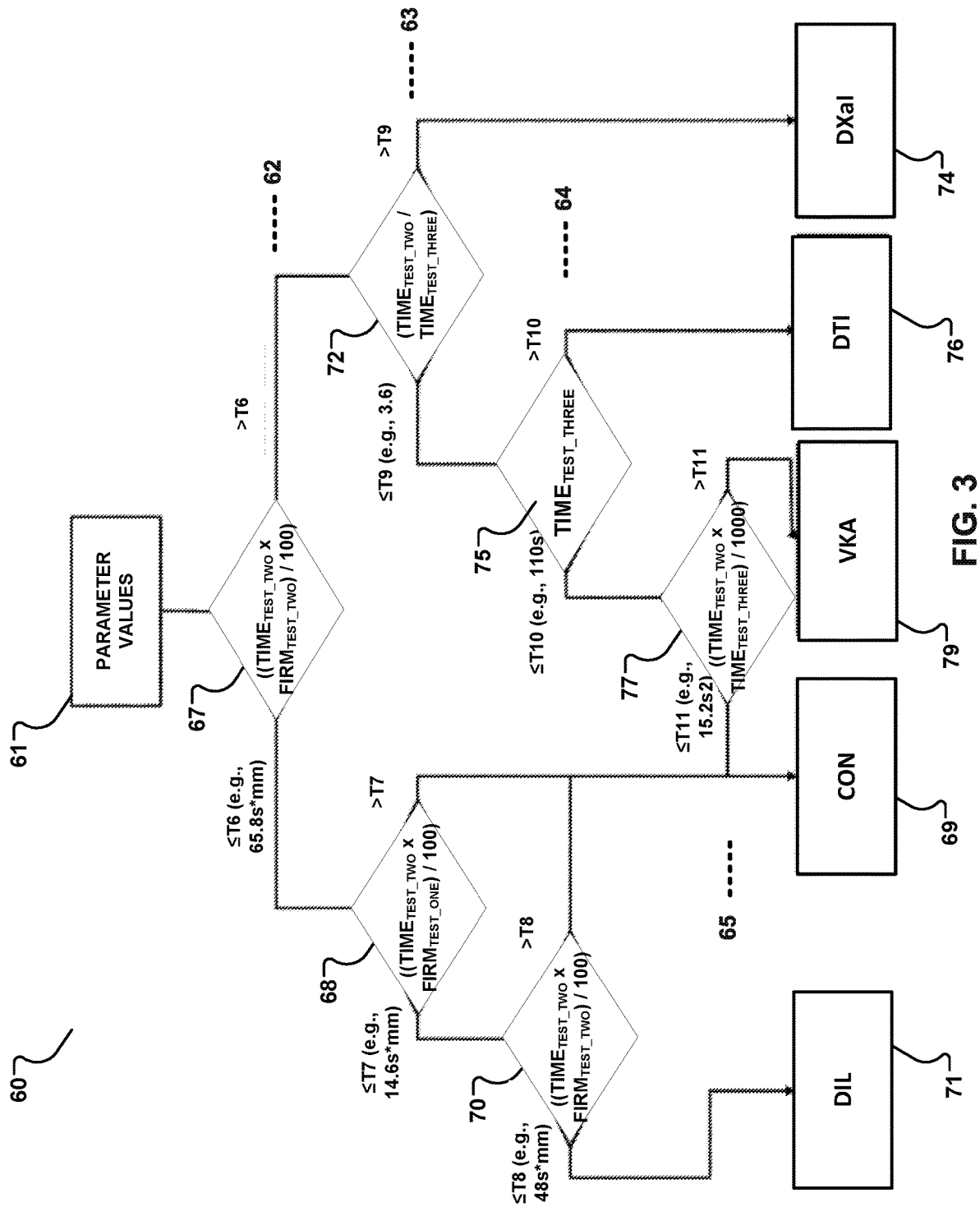
FIG. 3 is another example of a decision tree that is usable to implement comparisons used to differentiate among oral anticoagulants (such as VKAs, DXaIs and oral DTIs), IV DTIs, and/or coagulopathies and, possibly, to determine the presence of a particular anticoagulant class in a blood sample.
Figure 4:
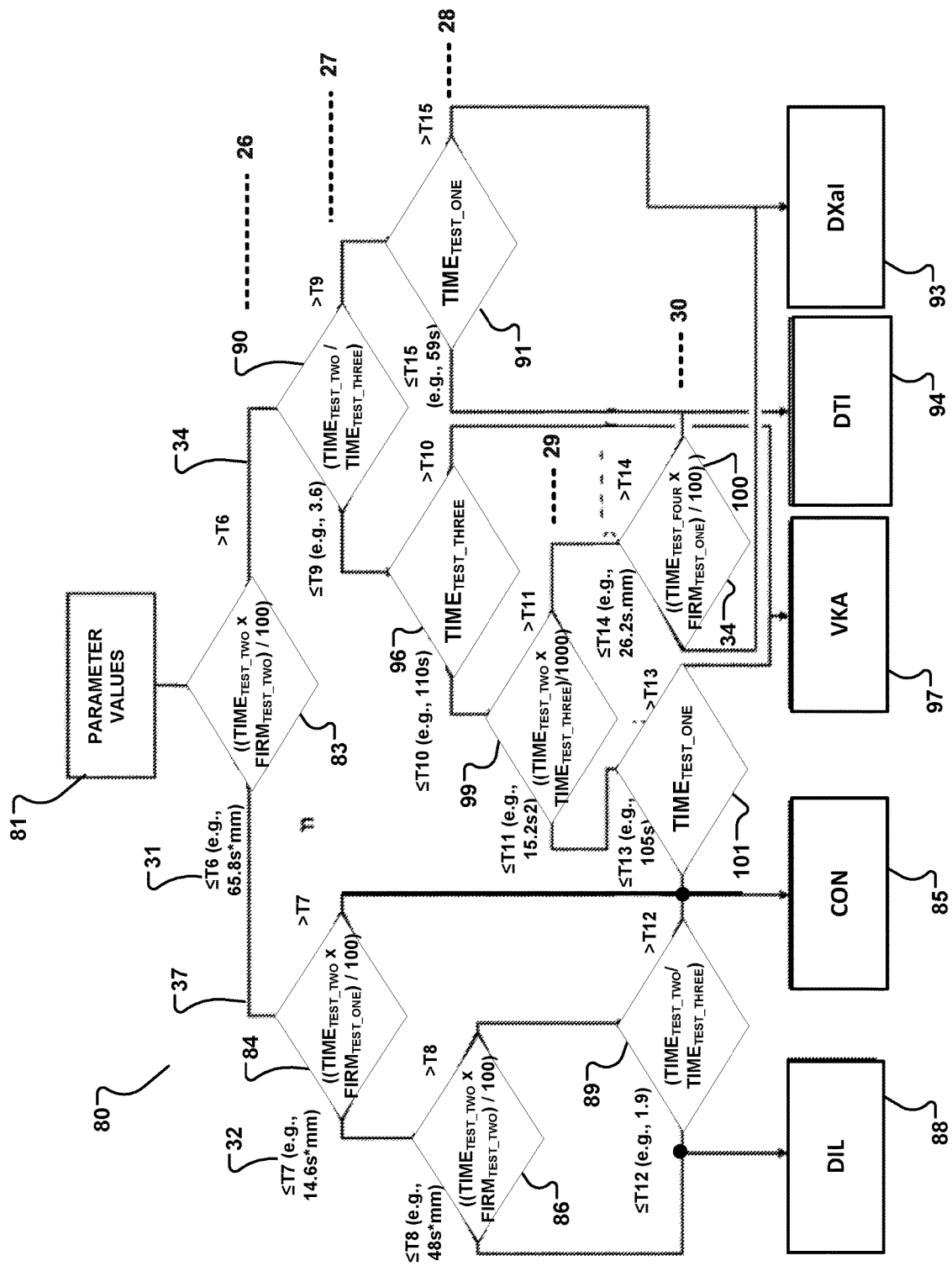
FIG. 4 is still another example of a decision tree that is usable to implement comparisons used to differentiate among anticoagulants (such as VKAs, DXaIs and oral DTIs), IV DTIs, and/or coagulopathies and, possibly, to determine the presence of a particular anticoagulant class in a blood sample.

FIGS. 2, 3, and 4 show examples of decision trees that use the parameters and values based on combinations of the parameters to perform the comparisons that are part of the processes. The example decision trees of FIGS. 2 to 4 may be constructed using machine learning processes based on training data from a set of patients. For example, a computing system may receive the training data and implement machine learning processes to construct a decision tree that produces results consistent with the training data. The decision tree may later be validated using a different set of validation data. In some implementations, the decision trees can be pre-structured, e.g., in terms of layers and/or operation sequences, and parameterized using the training data.

Each node of a decision tree is an operation based on one or more parameters, such as TIME or FIRM, for one or more of tests ONE through FIVE or a value based on a combination of parameters such as TIME or FIRM one or more of tests ONE through FIVE. Each node represents a decision as to which branch of the tree is to be followed based on operations on, e.g., a comparison of, the node's parameter or value to a predefined threshold (T). In FIG. 4 for example, processing proceeds to branch 37 if the input value to node 83 is less than or equal to threshold T6 31 and processing proceeds to branch 34 if the input value to node 83 is greater than the value of threshold T6. The thresholds may be cut-off values defined by an ROC curve analysis for each node of the decision tree. The thresholds may be user-provided or determined using a machine learning process. The threshold values can be adjusted using additional training data in a machine-learning process that generates the decision tree, for example. In some implementations, the magnitudes of the thresholds may change based on changes to the number and/or types of operations used to implement the processes. The processes described herein are not limited to any particular threshold values such as the examples shown.

As shown in the examples of FIGS. 2 to 4, different decision trees may include different numbers of levels. For example, in FIG. 4, there are five levels 26, 27, 28, 29, and 30. In this example, each level corresponds to decisions to be made along a branch of the decision tree. In some implementations, the machine learning processes may be configured to receive user input identifying and setting or limiting a number of levels to be included in a decision tree. This may be done in order to limit the complexity of the decision tree and, therefore, to limit or to reduce the time and/or computational resources (e.g., hardware resources such as memory) that it takes to arrive at decisions about the anticoagulants. In some implementations, the machine learning processes may be configured to establish the number of levels automatically based on the number of decisions that produces a best result.

The example decision trees shown in FIGS. 2 to 4 are used to detect, to monitor, and to differentiate among no coagulopathy (CON), DIL, VKAs (in the case of FIGS. 3 and 4), DTIs, and DXaI in a sample that includes blood. Referring to FIG. 1, the comparisons performed using the decision trees and/or ROC curve analyses result in detection (14) of an anticoagulant, a DTI, a coagulopathy, or no coagulopathy in the blood sample. Different decision trees having different parameters and thresholds may be used to detect different anticoagulants, such as VKAs, DXaIs and DTIs, and coagulopathies. The decision trees of FIGS. 2 to 4 are examples and the processes are not limited to those.

Example decision tree 35 of FIG. 2 is configured using parameters from viscoelastic tests to differentiate among anticoagulants, no coagulopathy (control/CON) and hemodilution (DIL). This example uses parameters from three tests TEST ONE, TEST FOUR, and TEST FIVE and combinations of parameters. Decision tree 35 is not configured to detect VKAs. $TIME_{TEST\_ONE}$ is used in decision tree 35. Decision tree 35 also uses combinations of parameters including the product of $TIME_{TEST\_FIVE}$ and $FIRM_{TEST\_ONE}$ 42 and the quotient of $TIME_{TEST\_FOUR}/FIRM_{TEST\_ONE}$ 44. The product of $TIME_{TEST\_FIVE}$ and $FIRM_{TEST\_ONE}$ 42 is scaled using a factor of 100 to enable comparison to T1.

Parameter values 40 from TEST ONE, TEST FOUR, and TEST FIVE are input at node 40. More specifically, parameters, such as TIME and FIRM, may be received from tests ONE, FOUR, and FIVE performed on a blood sample. At node 38, the process differentiates between DIL and other substances in the sample. If the value of $((TIME_{TEST\_FIVE} \times FIRM_{TEST\_ONE})/100)$ 42 is less than or equal to T1 (e.g., 8 s*mm (seconds-millimeters)), then processing proceeds along branch 41 indicating DIL 47 in the sample. If the value of $((TIME_{TEST\_FIVE} \times FIRM_{TEST\_ONE})/100)$ 43 is greater than T1, then processing proceeds along branch 45 to node 39.

At node 39, the process differentiates between no coagulopathy (CON) and an anticoagulant (e.g., VKA, DTI, or DXaI) in the sample. If $TIME_{TEST\_ONE}$ is ≤T2 (e.g., 82 s), then no coagulopathy—that is CON 48—is detected in the sample. If $TIME_{TEST\_ONE}$ is >T2, then processing proceeds to node 49. At node 49, the process differentiates between DXaI and other anticoagulants in the sample. If $TIME_{TEST\_ONE}$ is >T3 (e.g., 140.5 s), then DXaI 50 is detected in the sample. If $TIME_{TEST\_ONE}$ is ≤T3, processing proceeds to node 51. At node 51, the process differentiates between DTI and other anticoagulants in the sample. If $(TIME_{TEST\_FOUR}/FIRM_{TEST\_ONE})$ is >T4 (e.g., 20.4 s/mm), then DTI 53 is detected in the sample. At node 44, if $(TIME_{TEST\_FOUR}/FIRM_{TEST\_ONE})$ is ≤T4, then processing proceeds to node 55. At node 55, the process differentiates between DXaI and DTI in the sample. If $TIME_{TEST\_ONE}$ is ≤T5 (e.g., 88.5 s), then DTI 53 is detected in the sample. If $TIME_{TEST\_ONE}$ is >T5, then DXaI 50 is detected in the sample.

The example decision tree 60 of FIG. 3 is based on viscoelastic tests and parameters and includes parameters based on TEST TWO and TEST THREE, which are specific for detection of direct thrombin inhibitors (TEST THREE) and anticoagulants in general (TEST TWO).

Decision tree 60 receives parameter values 61, including TIME and FIRM from TEST ONE, TEST TWO, and TEST THREE performed on a sample. At node 67, the process determines whether there are anticoagulants in the sample. If $((TIME_{TEST\_TWO} \times FIRM_{TEST\_TWO})/100)$ is determined to be less than or equal to (≤) T6 (e.g., 68.5 s*mm), then it is determined that the sample does not contain anticoagulant. In this case, processing proceeds to node 68. At node 68, the process identifies no coagulopathy (CON) in the sample. If $((TIME_{TEST\_TWO} \times FIRM_{TEST\_ONE})/100)$ is >T7 (e.g., 14.6 s*mm), then no coagulotpathy CON 69 is detected. If $((TIME_{TEST\_TWO} \times FIRM_{TEST\_ONE})/100)$ is ≤T7, then processing proceeds to node 70. At node 70, the process differentiates between CON and DIL in the sample. At node 70, if $((TIME_{TEST\_TWO} \times FIRM_{TEST\_TWO})/100)$ is ≤T8 (e.g., 48 s*mm), then DIL 71 is detected in the sample. If $((TIME_{TEST\_TWO} \times FIRM_{TEST\_TWO})/100)$ is >T8, then no coagulopathy CON 69 is detected in the sample.

Referring back to node 67, if $((TIME_{TEST\_TWO} \times FIRM_{TEST\_TWO})/100)$ is determined to be greater than (>) T6 (e.g., 68.5 s*mm), then processing proceeds to node 72. At node 72, the process distinguishes DXaI in the sample. If $(TIME_{TEST\_TWO}/TIME_{TEST\_THREE})$ is >T9 (e.g., 3.6), then DXaI 74 is detected. If $(TIME_{TEST\_TWO}/TIME_{TEST\_THREE})$ is ≤T9, then processing proceeds to node 75. At node 75, the process distinguishes DTI in the sample. If $TIME_{TEST\_THREE}$ is >T10 (e.g., 110 s), then DTI 76 is detected. If $TIME_{TEST\_THREE}$ is ≤T10, then processing proceeds to node 77. At node 77, the process distinguishes between no coagulopathy and VKA in the sample. If $((TIME_{TEST\_TWO} \times TIME_{TEST\_THREE})/1000)$>T11 (e.g., 15.2 s²), then VKA 79 is detected. If $((TIME_{TEST\_TWO} \times TIME_{TEST\_THREE})/1000)$≤T11, then CON 69 is detected.

Referring to FIG. 4, in some cases, accuracy may be improved by including additional levels in the decision tree and thereby increasing the number of operations used to perform detection and differentiation. In this example, all tests and parameters from decision tree 60 are used, but the maximum tree depth is not limited, which results in a more complex and more branched decision tree. For example, the machine learning or other process that created the decision tree may have been programmed or allowed to use the number of levels that produced the best results.

Decision tree 80 uses parameters from four tests (tests ONE, TWO, THREE, and FOUR). That is, decision tree 80 is based on viscoelastic tests and parameters like in decision tree 35 including the modified tests TWO and THREE described above and parameters therefor like in decision tree 60. Decision trees 60 and 80 are comparable through levels 26 and 27 in FIG. 4. The difference is that decision tree 80 then uses TEST ONE and parameters based on $TIME_{TEST\_FOUR}$ and $FIRM_{TEST\_ONE}$ to achieve more accuracy in the detection of DTI. No coagulopathy and dilutional coagulopathy are also detected more accurately by including the ratio between $TIME_{TEST\_TWO}$ and $TIME_{TEST\_THREE}$ in the analysis. Unlike in decision tree 60, in decision tree 80, there are five levels.

Decision tree 80 include receiving parameter values 81 TIME and FIRM from TEST ONE, TEST TWO, TEST THREE, and TEST FOUR performed on a sample. At node 83, the process determines whether there are anticoagulants in the sample. If $((TIME_{TEST\_TWO} \times FIRM_{TEST\_TWO})/100)$ is determined to be less than or equal to ($\leq$) T6 (e.g., 68.5 s*mm), then processing proceeds to node 84. At node 84, the process determines whether the sample has been subjected to coagulopathy. If $((TIME_{TEST\_TWO} \times FIRM_{TEST\_ONE})/100)$ is >T7 (e.g., 14.6 s*mm), then the sample has not been subjected to coagulopathy CON 85. If $((TIME_{TEST\_TWO} \times FIRM_{TEST\_ONE})/100) \leq T7$, then processing proceeds to node 86. At node 86, the process determines whether the sample was subjected to DIL. If $((TIME_{TEST\_TWO} \times FIRM_{TEST\_TWO})/100)$ is $\leq T8$ (e.g., 48 s*mm), then DIL 88 is detected. If $((TIME_{TEST\_TWO} \times FIRM_{TEST\_TWO})/100)$ is >T8, then processing proceeds to node 89. At node 89, the process determines whether the sample has been subjected to DIL or the sample has not been subjected to coagulopathy (CON). If $(TIME_{TEST\_TWO}/TIME_{TEST\_THREE})$ is $\leq T12$ (e.g., 1.9), then DIL 88 is detected. If $(TIME_{TEST\_TWO}/TIME_{TEST\_THREE})$ is >T12, then the sample has not been subjected to coagulopathy CON 85. Note that nodes 83, 84 and 86 are identical to corresponding nodes 67, 68, and 70 of decision tree 60 (FIG. 3), but an additional node 89 has been added to the decision tree analysis of FIG. 4 because the number of levels in decision tree 80 have not been constrained.

Referring back to node 83, if $((TIME_{TEST\_TWO} \times FIRM_{TEST\_TWO})/100)$ is determined to be greater than (>) T6, then processing proceeds to node 90. At node 90, if $(TIME_{TEST\_TWO}/TIME_{TEST\_THREE})$ is >T9 (e.g., 3.6), then processing proceeds to node 91. At node 91, the process determines whether DXaI or VKA is in the sample. At node 91, if $TIME_{TEST\_ONE}$ is >T15 (e.g., 59 s), then DXaI 93 is detected. If $TIME_{TEST\_ONE}$ is $\leq T15$, then DTI 94 is detected.

Referring back to node 90, If $(TIME_{TEST\_TWO}/TIME_{TEST\_THREE})$ is $\leq T9$, then processing proceeds to node 96. At node 96, the process determines whether DTI is in the sample. In node 96, if $TIME_{TEST\_THREE}$ is >T10 (e.g., 110 s), then DTI 97 is detected. If $TIME_{TEST\_THREE}$ is $\leq T10$, then processing proceeds to node 99. In node 99, if $((TIME_{TEST\_TWO} \times TIME_{TEST\_THREE})/1000)$>T11 (e.g., 15.2 s$^2$), then processing proceeds to node 100. At node 100, the process determines whether the sample contains DXaI or DTI. In node 100, if $((TIME_{TEST\_FOUR} \times FIRM_{TEST\_ONE})/100)$>T14 (e.g., 26.2 s·mm), then DTI 94 is detected. If $((TIME_{TEST\_FOUR} \times FIRM_{TEST\_ONE})/100) \leq T14$, then DXaI 93 is detected.

Referring back to node 99, if $((TIME_{TEST\_TWO} \times TIME_{TEST\_THREE})/1000) \leq T11$, then processing proceeds to node 101. At node 101, the process determines whether the sample contains VKA or has not been subjected to coagulopathy. In node 101, if $TIME_{TEST\_ONE}$ is >T13 (e.g., 105 s), then VKA 97 is detected. If $TIME_{TEST\_ONE}$ is $\leq T13$, then the sample has not been subjected to coagulopathy—CON 85. Note that nodes 90, 96, and 99 of decision tree 80 are identical to corresponding nodes 72, 75, and 77 of decision tree 60, but additional operations have been added to decision tree 80 because the number of levels in decision tree 80 have not been constrained.

As previously explained, the parameters used for comparison may be obtained from a viscoelastic testing system. Components of an example viscoelastic testing system include an analyzer instrument. The analyzer instrument may include, or be in communication with, a computing system. The analyzer instrument or computing system may include machine-readable memory that stores executable instructions, and one or more processing devices to execute the instructions to implement all or part of the processes, such as the decision tree analyses.

The tests that produce the parameters described herein may be performed using a viscoelastic testing system having a cartridge containing chambers in which the different tests are implemented and performed automatically, e.g., under software control. The cartridge may fit within the analyzer instrument, for example. The tests may be performed using tactile techniques such as ROTEM® rotational detection or non-tactile techniques, such as ultrasound detection, optical detection, or a combination thereof. In another example, the tests may be implemented manually using a panel of assays. In whatever way the tests are performed, the tests produce parameters, such as those described herein, which are used by the processes to detect, to differentiate, and to monitor of one or more anticoagulants, coagulopathies, or lack thereof in a blood sample.

The parameters may also be used to identify the type anticoagulants or coagulopathies in a blood sample. For example, the processes may include detecting the amount—for example, the dosage—of DXaIs, DTIs, VKAs, and DIL in a blood sample. Following detection and differentiation, known techniques may be used to detect the amounts in the blood sample. If the exact DOAC or IV DTI is known, a semi-quantitative determination of the corresponding drug plasma concentration can be performed. This applies for DOACs (e.g., DXaIs and the DTI dabigatran) and IV DTIs, e.g., argatroban and bivalirudin. This may not apply for VKAs since they do not directly inhibit coagulation factors, but they inhibit the synthesis of the so call vitamin K-dependent coagulation factors II, VII, IX and X. Therefore, plasma concentrations of VKAs are not measured, but instead but their effect on INR (normalized ratio) are measured. The ROTEM® assay EXTEM CT parameter again provides a good correlation with INR (r>0.9) in patients treated with VKAs. In another example, if the anticoagulant is known, plasma concentrations of the DOAC or DTI correlate with the CT values of ROTEM® assays. ECATEM CT prolongations are specific for DTIs. TFTEM CT prolongation is more sensitive to oral anticoagulants compared to FIBTEM, EXTEM or HEPTEM CT and may be used to identify oral anticoagulants, particularly in low concentrations or anticoagulants with minor effect of clotting times (e.g., apixaban).

Assessment of DOAC concentrations may be affected by hemodilution or other coagulopathies at the same time—but this is also be true for calibrated DOAC assays. Therefore, the term semi-quantitative determination of blood concentrations might be most appropriate as used above. Since ROTEM® is working with whole blood, blood concentrations are measured directly and not plasma concentrations. However, this can be corrected using hematocrit.

Referring to FIG. 1, the processes may generate data for a user interface to display detected anticoagulants, such as VKAs, FDXaIs and DTIs, coagulopathies, or lack thereof in a blood sample. The data may be used to display (15) the detection result at the point-of-care, for, example, on a display screen of the analyzer instrument.

After the anticoagulant is detected, a reversal agent (16) can be administered to the patient to reverse the effects of the anticoagulant. For example, idarucizumab for reversal of dabigatran, or andexanet alfa for reversal of apixaban or rivaroxaban may be administered. Any necessary medical procedures, such as surgery, can then be performed without, or with reduced, fear of excessive patient bleeding. In some implementations, the display device may display an identity of the reverse agent based on the type of anticoagulant that was detected by the processes. In some implementations, the display device may display instructions on how to address the anticoagulant that was detected by the processes.

The numerical values used in the processes described herein are examples only; other numerical values may be used. For each numerical value, a range of values, as opposed to a specific value, can be used. Additionally, the decision trees shown in the figures are examples; other decision trees having different numerical values, nodes, numbers of nodes, or numbers of levels may be used. The decision trees can be used to implement to make other measurements or decisions. Also, variations of these decision trees, e.g., based on availability of test or measurement data, can be used to similarly support decision making in situations similar to those described herein.

In another example of the processes, dilutional coagulopathy (DIL) was simulated in-vitro, and two standardized conditions were used. In some situations, trauma-induced coagulopathy can be much more complex, highly variable, and influenced by additional factors other than hemodilution, such as endothelial integrity, glycocalyx shedding, endogenous heparinoids, temperature, acidosis, and platelet dysfunction. The processes can be adapted or modified to address these situations.

Also, the processes herein may apply to the entire range of plasma concentrations in a blood sample.

The processes may be implemented using computing systems or any other appropriate computing device. Systems and processes can be implemented, at least in part, using one or more computer program products, e.g., one or more computer program tangibly embodied in one or more information carriers, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the processes can be performed by one or more programmable processors executing one or more computer programs to perform the functions described herein. All or part of the processes can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random-access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks. Machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

The processes can run on an embedded system of a testing device such as the viscoelastic testing devices described herein, a processor in the clinical environment to which the testing values are sent, or a processor on a remote location (e.g., on a cloud, a private, or a public network or device) to which the testing values are sent.

Elements of different implementations described herein may be combined to form other implementations not specifically set forth above. Elements may be left out of the structures described herein without adversely affecting their operation. Furthermore, various separate elements may be combined into one or more individual elements to perform the functions described herein.

What is claimed is:

1. A method detecting a presence of one or more oral anticoagulants or intravenous (IV) direct thrombin inhibitors in a blood sample, the method comprising:
   receiving parameters that are based on viscoelastic tests;
   comparing the parameters to predefined threshold values, the parameters and the predefined threshold values being based on an identity of the one or more oral anticoagulants or the IV direct thrombin inhibitors; and
   detecting, based on the comparing, the presence of the one or more oral anticoagulants or IV direct thrombin inhibitors in the blood sample;
   wherein the viscoelastic tests are performed on portions of the blood sample to obtain the parameters, the viscoelastic tests comprising both a viscoelastic test based on Ecarin activation and a viscoelastic test with low tissue factor activation.

2. The method of claim 1, wherein the one or more oral anticoagulants comprise a direct factor Xa inhibitor; and
   wherein detecting comprises detecting the direct factor Xa inhibitor.

3. The method of claim 1, wherein the one or more oral anticoagulants comprise a vitamin K-antagonist; and
   wherein detecting comprises detecting the vitamin K-antagonist.

4. The method of claim 1, wherein detecting comprises determining that the blood sample has been subjected to hemodilution.

5. The method of claim 1, wherein detecting, based on the comparing, comprises performing a receiver operating characteristic (ROC) curve analyses based on the parameters.

6. The method of claim 1, wherein detecting, based on the comparing, comprises performing a decision tree analysis based on the parameters.

7. The method of claim 1, wherein the decision tree analysis is performed using a decision tree, the decision tree being based, at least in part, on the parameters and on combinations of the parameters.

8. The method of claim 7, wherein the combinations of the parameters are user-provided.

9. The method of claim 7, wherein the decision tree is generated using machine learning.

10. The method of claim 7, wherein the decision tree comprises multiple levels, where a number of the multiple levels are generated automatically based on external input.

11. The method of claim 1, further comprising:
generating data for a user interface to display detected oral anticoagulants or IV direct thrombin inhibitors.

12. The method of claim 1, wherein the viscoelastic tests are performed using a cartridge having multiple chambers, each of the portions of the blood sample being received in one of the multiple chambers, and each of the multiple chambers for performing a viscoelastic test on a corresponding portion of the blood sample.

13. The method of claim 1, wherein the parameters enable differentiation at greater than a predetermined level of accuracy.

14. The method of claim 13, wherein the predetermined level of accuracy is at least 70%.

15. A system for detecting a presence of one or more oral anticoagulants or IV direct thrombin inhibitors in a blood sample, the system comprising:
one or more processing devices; and
non-transitory machine-readable storage storing instructions that are executable by the one or more processing devices to perform operations comprising:
receiving parameters that are based on viscoelastic tests;
comparing the parameters to predefined threshold values, the parameters and the predefined threshold values being based on an identity of the one or more oral anticoagulants or the IV direct thrombin inhibitors; and
detecting, based on the comparing, the presence of the one or more oral anticoagulants or IV direct thrombin inhibitors in the blood sample;
wherein the viscoelastic tests are performed on portions of the blood sample to obtain the parameters, the viscoelastic tests comprising both a viscoelastic test based on Ecarin activation and a viscoelastic test with low tissue factor activation.

16. The system of claim 15, wherein the one or more oral anticoagulants comprise a direct factor Xa inhibitor; and
wherein detecting comprises detecting the direct factor Xa inhibitor.

17. The system of claim 15, wherein the one or more oral anticoagulants comprise a vitamin K-antagonist; and
wherein detecting comprises detecting the vitamin K-antagonist.

18. The system of claim 15, wherein detecting comprises determining that the blood sample has been subjected to hemodilution.

19. The system of claim 15, wherein detecting, based on the comparing, comprises performing receiver operating characteristic (ROC) curve analyses based on the parameters.

20. The system of claim 15, wherein detecting, based on the comparing, comprises performing a decision tree analysis based on the parameters; and
wherein the decision tree analysis is implemented using a decision tree, the decision tree being based, at least in part, on the parameters and combinations of the parameters.

* * * * *